(12) United States Patent
Walker et al.

(10) Patent No.: US 9,629,595 B2
(45) Date of Patent: Apr. 25, 2017

(54) SYSTEMS AND METHODS FOR LOCALIZING, TRACKING AND/OR CONTROLLING MEDICAL INSTRUMENTS

(71) Applicant: Hansen Medical, Inc., Mountain View, CA (US)

(72) Inventors: Sean Walker, Mountain View, CA (US); Christopher Sewell, Sunnyvale, CA (US); June Park, Palo Alto, CA (US); Prabu Ravindran, Milpitas, CA (US); Aditya Koolwal, Mountain View, CA (US); Dave Camarillo, Aptos, CA (US); Federico Barbagli, San Francisco, CA (US)

(73) Assignee: Hansen Medical, Inc., Mountain View, CA (US)

( * ) Notice: Subject to any disclaimer, the term of this patent is extended or adjusted under 35 U.S.C. 154(b) by 798 days.

(21) Appl. No.: 13/832,586

(22) Filed: Mar. 15, 2013

(65) Prior Publication Data
US 2014/0275985 A1 Sep. 18, 2014

(51) Int. Cl.
| | |
|---|---|
| *A61B 6/00* | (2006.01) |
| *A61B 5/06* | (2006.01) |
| *A61B 6/12* | (2006.01) |
| *A61B 34/20* | (2016.01) |
| *A61B 5/00* | (2006.01) |
| *A61B 34/30* | (2016.01) |
| *A61B 90/00* | (2016.01) |

(52) U.S. Cl.
CPC .............. *A61B 6/485* (2013.01); *A61B 5/062* (2013.01); *A61B 5/066* (2013.01); *A61B 6/12* (2013.01); *A61B 34/20* (2016.02); *A61B 34/30* (2016.02); *A61B 5/725* (2013.01); *A61B 2034/2051* (2016.02); *A61B 2034/301* (2016.02); *A61B 2090/376* (2016.02)

(58) Field of Classification Search
CPC ..... A61B 19/5244; A61B 5/062; A61B 5/066; A61B 6/12; A61B 6/485; A61B 19/2203; A61B 5/725; A61B 2019/2211; A61B 2019/5238; A61B 2019/5251
See application file for complete search history.

(56) References Cited

U.S. PATENT DOCUMENTS

| | | | |
|---|---|---|---|
| 5,398,691 | A | 3/1995 | Martin et al. |
| 5,408,409 | A | 4/1995 | Glassman et al. |
| 5,524,180 | A | 6/1996 | Wang et al. |
| 5,631,973 | A | 5/1997 | Green |
| 5,713,946 | A | 2/1998 | Ben-Haim |
| 5,749,362 | A | 5/1998 | Funda et al. |
| 5,859,934 | A | 1/1999 | Green |
| 5,876,325 | A | 3/1999 | Mizuno et al. |
| 5,951,475 | A | 9/1999 | Gueziec et al. |
| 6,226,543 | B1 | 5/2001 | Gilboa et al. |
| 6,259,806 | B1 | 7/2001 | Green |
| 6,272,371 | B1 | 8/2001 | Shlomo |

(Continued)

FOREIGN PATENT DOCUMENTS

WO 03086190 A1 10/2003

*Primary Examiner* — Bo J Peng
(74) *Attorney, Agent, or Firm* — Knobbe, Martens, Olson & Bear, LLP

(57) ABSTRACT

Systems and methods are described herein for tracking, localization or controlling an elongate instrument or other medical instrument in an image or patient.

27 Claims, 24 Drawing Sheets

(56) References Cited

U.S. PATENT DOCUMENTS

| | | | |
|---|---|---|---|
| 6,424,885 B1 | 7/2002 | Niemeyer et al. | |
| 6,726,675 B1 | 4/2004 | Beyar | |
| 7,155,315 B2 | 12/2006 | Niemeyer et al. | |
| 2006/0025676 A1 | 2/2006 | Viswanathan et al. | |
| 2006/0058643 A1* | 3/2006 | Florent | A61B 6/481 600/423 |
| 2006/0098851 A1* | 5/2006 | Shoham | A61B 17/1703 382/128 |
| 2008/0118118 A1* | 5/2008 | Berger | G06K 9/342 382/128 |
| 2008/0161681 A1* | 7/2008 | Hauck | A61B 5/06 600/424 |
| 2010/0054536 A1* | 3/2010 | Huang | G06K 9/32 382/103 |
| 2010/0161022 A1* | 6/2010 | Tolkowsky | G06T 7/0022 623/1.11 |

* cited by examiner $$^M_T T = ^H_R T \, ^R_T T$$

$$= \begin{pmatrix} ^M_R R & ^R_T d \\ 0 & 1 \end{pmatrix} \begin{pmatrix} ^R_T R & ^R_T d \\ 0 & 1 \end{pmatrix}$$

$$\begin{pmatrix} ^H_R R (^T_R R)^T & ^H_R R (^T_R R)^T (-^T_R d) + ^M_R d \\ 0 & \end{pmatrix}$$

$$^M_R T = \begin{pmatrix} ^M_R R & ^M_T d \\ 0 & 1 \end{pmatrix}$$

SYSTEMS AND METHODS FOR LOCALIZING, TRACKING AND/OR CONTROLLING MEDICAL INSTRUMENTS

FIELD OF THE INVENTION

The systems and methods described herein relate generally to medical instruments, such as elongate steerable instruments for minimally-invasive intervention or diagnosis, and more particularly to methods, systems, and apparatus for controlling, localizing or tracking the location, position, orientation and/or shape of one or more parts of a medical instrument.

BACKGROUND

Currently known minimally invasive procedures for diagnosis and treatment of medical conditions use shapeable instruments, such as steerable devices, flexible catheters or more rigid arms or shafts, to approach and address various tissue structures within the body. For various reasons, it is highly valuable to be able to determine the 3-dimensional spatial position of portions of such shapeable instruments relative to other structures, such as the operating table, other instruments, or pertinent anatomical tissue structures.

There remains a need to apply the information gained by the spatial or shape information of a medical instrument and applying this information to produce improved device control or improved modeling when directing a robotic or similar device. There also remains a need to apply such controls to medical procedures and equipment.

SUMMARY

In certain variations, a method of controlling a robotically controlled elongate instrument in real time may include one or more of the following steps: displaying an image of an anatomy of a patient; tracking or detecting a localization sensor coupled to the robotically controlled elongate instrument; and registering localization data from the localization sensor to the image to provide a continuously updated location of at least a portion of the elongate instrument in the image of the anatomy of a patient to facilitate robotic navigation of the elongate instrument through the anatomy.

In certain variations, a system for tracking or localizing a robotically controlled elongate instrument may include: an image of an anatomy of a patient; an electromagnetic localization sensor coupled to an elongate instrument; and/or an electromagnetic field generator. The generator may be configured to produce an electromagnetic field in which the electromagnetic localization sensor is detected. The localization sensor may provide localization data for at least a portion of the elongate instrument, where the localization data may be registered to the image to provide a continuously updated location of at least a portion of the elongate instrument in the image. This may facilitate robotic navigation of the elongate instrument through the anatomy.

In certain variations, a system for tracking or localizing a robotically controlled elongate instrument may include: an image of an anatomy of a patient; an electromagnetic localization sensor coupled to an elongate instrument; an electromagnetic field generator; and/or at least one reference sensor, e.g., fixed reference sensor, positioned in a workspace of the electromagnetic field generator. The electromagnetic field generator may be movable relative to the reference sensor thereby expanding the workspace for elongate instrument tracking.

In certain variations, a method of tracking or localizing a robotically controlled elongate instrument in real time may include one or more of the following steps: displaying a single image of an anatomy of a patient; tracking or detecting a localization sensor coupled to the robotically controlled elongate instrument; and/or registering localization data from the localization sensor to the image via a reference sensor to provide a continuously updated location of at least a portion of the elongate instrument in the image of the anatomy of a patient to facilitate robotic navigation of the elongate instrument through the anatomy.

In certain variations, a medical system for controlling an elongate instrument may include a robotically controlled instrument assembly comprising a shapeable elongate instrument. The system may include a localization system coupled to the robotically controlled instrument assembly and configured to track the shapeable elongate instrument, where at least a portion of the localization system is sterilely isolated from the robotically controlled instrument assembly.

In certain variations, a system or robotic system for controlling an elongate instrument with respect to a target space may include an elongate instrument having a localization sensor coupled thereto. The system may include a robotic drive system including at least one actuator, where the robotic drive system is configured to interchangeably couple with the elongate instrument to position the instrument with respect to the target space. The system may also include a controller configured to produce a registration between a localization sensor frame and an image frame or a patient frame. The controller can produce a plurality of signals to direct the robotic drive system or elongate instrument in the image frame using the registration and the image may include an image of the target space or patient.

In certain variations, a robotic system for controlling an elongate instrument with respect to a target space may include an elongate instrument having a localization sensor coupled thereto. The system may include a robotic drive system having at least one actuator. The robotic drive system may be configured to interchangeably couple with the elongate instrument to position the instrument with respect to the target space. The system may include a controller configured to register localization data from the localization sensor to an image of an anatomy or to a patient or target space frame to provide a continuously updated location of at least a portion of the elongate instrument in the image. The controller can produce a plurality of signals to direct robotic navigation of the elongate instrument through the anatomy based on the location of at least a portion of the elongate instrument in the image.

In certain variations, a method of tracking an elongate instrument in real time in an image may include one or more of the following steps: initializing an active contour in the image where the active contour corresponds to at least a portion of the elongate instrument; and updating the active contour as the elongate instrument moves by performing a search based on pixel intensity to track the elongate instrument.

In certain variations, a method of tracking a robotically controlled elongate instrument in real time in an image includes one or more of the following steps: controlling movement of the elongate instrument with a robotic or system command; creating an active contour which corresponds to at least a portion of the elongate instrument; updating the active contour as the elongate instrument moves; performing an image-based or template matching search along the active contour to track features of the elongate instrument; and/or predicting elongate instrument movement based on the commanded elongate instrument motion to increase tracking accuracy.

In certain variations, a system or robotic system for controlling an elongate instrument with respect to a target space is provided. The system may include a robotic drive system having at least one actuator. The robotic drive system may be configured to interchangeably couple with the elongate instrument to position the instrument with respect to the target space. The system may include a controller configured to initialize an active contour in an image, where the active contour corresponds to at least a portion of the elongate instrument. The controller may be configured to update the active contour as the elongate instrument moves by performing a search based on pixel intensity. The controller can produce a plurality of signals to direct the robotic drive system or elongate instrument in the image frame based on tracking of the elongate instrument with the active contour.

In certain variations, systems, methods, and devices described herein may include a robotic medical system for controlling a shapeable elongate instrument within an anatomical region. The systems, methods, and devices described herein may incorporate localization or tracking systems for controlling the shapeable elongate instrument and/or for performing other tasks related to controlling the instrument (e.g., improving a map or a model of the anatomy or region).

Other and further embodiments, objects and advantages of the invention will become apparent from the following detailed description when read in view of the accompanying figures.

DETAILED DESCRIPTION

Figure 1:
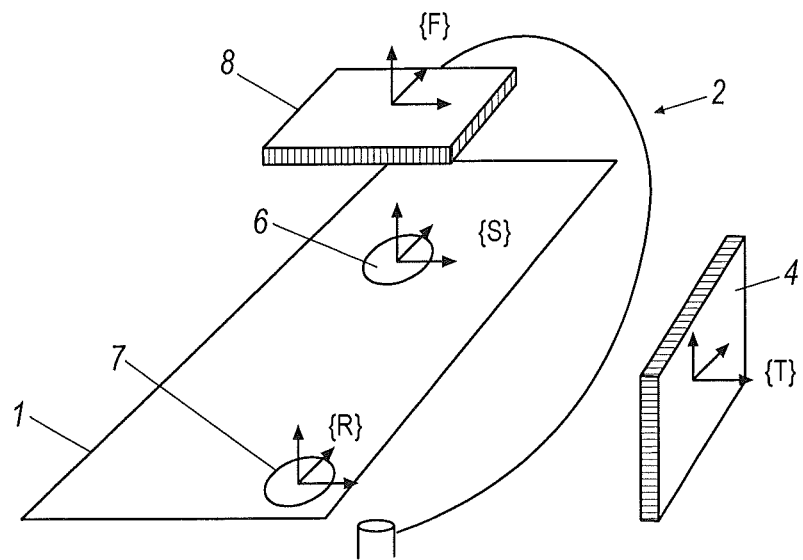
FIG. 1 illustrates a variation of a localization system in a typical operation room set up.
Figure 1:
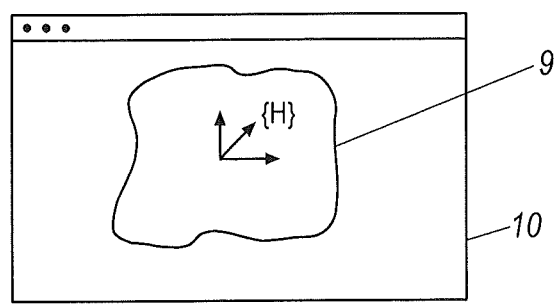

Various localization systems and methods for tracking, performing localization of, and/or controlling an elongate instrument, e.g., a robotically controlled elongate instrument, in real time, in a clinical or other environment, are described herein. Various elongate instruments are contemplated for use in the various systems described herein, e.g., a catheter or vascular catheter. The various methods and systems may include integrating or registering a localization system or a localization sensor coupled to an elongate instrument, with an image. A Traxtal electromagnetic tracking or localization system is one example of a system that allows for the tracking of a location, position and/or orientation of a localization sensor placed in a pulsating electromagnetic or magnetic field. Various localization sensors may be utilized, e.g., electromagnetic sensors, fiber optic sensors, and other sensors for detecting or controlling the movement of medical equipment. When the localization sensor is integrated into an image, it enhances the capabilities of an elongate instrument control or tracking system by allowing a user or doctor to easily navigate the elongate instrument through the complex anatomy without exposing the patient to excessive radiation over a prolonged period of time.

The localization data or tracking information of a localization sensor may be registered to the desired image or model in order for navigation of an elongate instrument through the image or model to accurately represent movement of the elongate instrument. The registration process often requires information about the imaging system providing the image, such as its physical dimensions and/or the details about the imaging techniques used to acquire a particular 3D model or other image. Due to the variability in equipment used in a clinical environment, in certain situations there may be no guarantee that such information will be available or easily obtainable to an outside party. As such, various robust techniques to estimate system parameters and various registration techniques may help facilitate the clinical use of localization technology.

In certain variations, a method for tracking, localizing or controlling a robotically controlled elongate instrument in real time may include displaying an image of a patient's anatomy. A localization sensor may be coupled to the robotically controlled elongate instrument. The localization sensor may provide localization data of the sensor and/or elongate instrument. The localization data from the localization sensor may be registered to the image. Registering may include transforming localization data generated by the localization sensor to the coordinate system of the image such that localization data of the elongate instrument, to which the localization sensor is coupled, is overlaid on the image. The coordinate system of the localization sensor may be transformed or translated to the coordinate system of the image through one or more transformations, and optionally through other coordinate systems, to register the localization data to the image. As a result, a continuously or substantially continuously updated location of at least a portion of the elongate instrument is provided in the image of the anatomy of a patient, which allows for or facilitates robotic navigation or control of the elongate instrument through the anatomy e.g., through the vasculature of a patient.

The location, position and/or orientation of the localization sensor may be continuously tracked to allow for accurate manipulation of the elongate instrument in or through the anatomy of a patient. Various types of images may be utilized in the methods and systems described herein. For example, an image may be generated by CT or 2D or 3D fluoroscopy. An image may include a 3D or 2D anatomical model or a 2D or 3D fluoroscopic image or other types of images useful for visualizing an anatomy of a patient to perform various medical procedures.

When using a fluoroscopy image, an image intensifier may be utilized. Localization data from the localization sensor may be registered to a fluoroscopy coordinate system of a fluoroscopy image coupled to the image intensifier. In order to register the localization data from the localization sensor to the fluoroscopy image, various parameters may be ascertained or known. For example, such parameters may include: a distance from an X-ray source to the image intensifier, a distance from the source to a bed, a size of the image intensifier, and/or the axis of rotation of a c-arm of the fluoroscopy system.

In certain variations, the localization sensor may include an electromagnetic localization sensor. The electromagnetic localization sensor may be placed in a pulsating magnetic field generated by an electromagnetic field generator or transmitter to allow for detection or tracking of the localization sensor.

In certain variations, a system for tracking, localizing or controlling a robotically controlled elongate instrument may include an image of an anatomy of a patient, an electromagnetic localization sensor coupled to an elongate instrument, and an electromagnetic field generator. The image may be displayed, generated or otherwise received by the system. The electromagnetic field generator may produce an electromagnetic field in which the electromagnetic localization sensor is detected. The localization sensor may provide localization data for at least a portion of the elongate instrument. The localization data is registered to the image by performing one or more transformations to provide a continuously or substantially continuously updated location of at least a portion of the elongate instrument in the image. This facilitates or allows for robotic navigation or control of the elongate instrument through the anatomy, e.g., through the vasculature of a patient.

Various types of images may be utilized in the methods and systems described herein. For example, an image may be generated by CT or 2D or 3D fluoroscopy. An image may include a 3D or 2D anatomical model or a 2D or 3D fluoroscopic image or other types of images useful for visualizing an anatomy of a patient to perform various medical procedures.

A location, position and/or orientation of the localization sensor is measureable in a coordinate system of the electromagnetic field generator. The location, position and/or orientation measurement of the localization sensor may be registered to the image via one or more transformations.

When using a fluoroscopy image, an image intensifier may be utilized. Localization data from the localization sensor may be registered to a fluoroscopy coordinate system of a fluoroscopy image coupled to the image intensifier. In order to register the localization data from the localization sensor to the fluoroscopy image, various parameters may be ascertained or known. For example, such parameters may include: a distance from an X-ray source to the image intensifier, a distance from the source to a bed, a size of the image intensifier, and/or the axis of rotation of a c-arm of the fluoroscopy system.

In another variation, a system for tracking, localizing or controlling a robotically controlled elongate instrument may include an image of an anatomy of a patient, an electromagnetic localization sensor coupled to an elongate instrument, an electromagnetic field generator; and one or more reference sensors, e.g., fixed reference sensors, positioned in a workspace of the electromagnetic field generator. The electromagnetic field generator may be movable relative to the reference sensor thereby extending or expanding the workspace for elongate instrument tracking or in which the elongate instrument may be tracked. The reference sensor provides a reference coordinate system that is independent of the placement of the electromagnetic field generator.

The localization sensor provides localization data for at least a portion of the elongate instrument. The localization data is registered to the image via the reference coordinate system, to provide a continuously or substantially continuously updated location of at least a portion of the elongate instrument in the image. This facilitates or allows robotic navigation of the elongate instrument through the anatomy.

A location, position and/or orientation of the localization sensor may be measured in the reference sensor coordinate system. The location, position and/or orientation measurement of the localization sensor is registered to the image via one or more transformations. In one example, a transformation may be fixed in space and may not require online computation. The electromagnetic field generator may be moved or rotated without distorting a measurement of the localization sensor as the localization sensor is measured in the reference sensor coordinate system.

In certain variations, the reference sensor may include an anatomy patch. The anatomy patch may be positioned on a patient such that the reference sensor appears in the image. As the reference sensor appears in the image, a location, position and/or orientation of the reference sensor can be measured in the coordinate system of the image.

Various types of images may be utilized in the methods and systems described herein. For example, an image may be generated by CT or 2D or 3D fluoroscopy. An image may include a 3D or 2D anatomical model or a 2D or 3D fluoroscopic image or other types of images useful for visualizing an anatomy of a patient to perform various medical procedures.

A location, position and/or orientation of the localization sensor is measurable in a coordinate system of the electromagnetic field generator. The location, position and/or orientation measurement of the localization sensor may be registered to the image via one or more transformations.

When using a fluoroscopy image, an image intensifier may be utilized. Localization data from the localization sensor may be registered to a fluoroscopy coordinate system of a fluoroscopy image coupled to the image intensifier. In order to register the localization data from the localization sensor to the fluoroscopy image, various parameters may be ascertained or known. For example, such parameters may include: a distance from an X-ray source to the image intensifier, a distance from the source to a bed, a size of the image intensifier, and/or the axis of rotation of a c-arm of the fluoroscopy system.

In certain variations, a method of tracking, localizing or controlling a robotically controlled elongate instrument in real time may include: displaying a single image of an anatomy of a patient; tracking a localization sensor coupled to the robotically controlled elongate instrument; and registering localization data from the localization sensor to the image via one or more fixed reference sensors to provide a continuously updated location of at least a portion of the elongate instrument in the image of the anatomy of a patient to facilitate robotic navigation of the elongate instrument through the anatomy. Only a single image may be required to register the localization data. A location, position and/or orientation measurement of the localization sensor may be registered to the image via one or more transformations. A fluoroscope for creating the displayed image may remain fixed and may not be required to rotate or move to complete the registration. In variations where an electromagnetic localization sensor is utilized, the electromagnetic field generator may be movable relative to the fixed reference sensor, thereby expanding the workspace for elongate instrument tracking or in which the elongate instrument may be tracked.

In certain variations, a localization system as described herein may include two subsystems, an imaging subsystem and a tracking subsystem. The imaging subsystem is used to acquire and visualize patient data. For example, a CT scan may provide a 3D model of the patient's anatomy and a fluoroscopy imaging system may provide an X-ray view of the patient's anatomy during an operation. The tracking subsystem continuously tracks the location, position and/or orientation of the sensor, allowing the doctor to manipulate the elongate instrument or tool to which the sensor is coupled, with ease. The two subsystems are put together via a registration process, which transforms the localization or tracking data so that it appears correctly when overlayed on top of the acquired image.

Figure 16A:
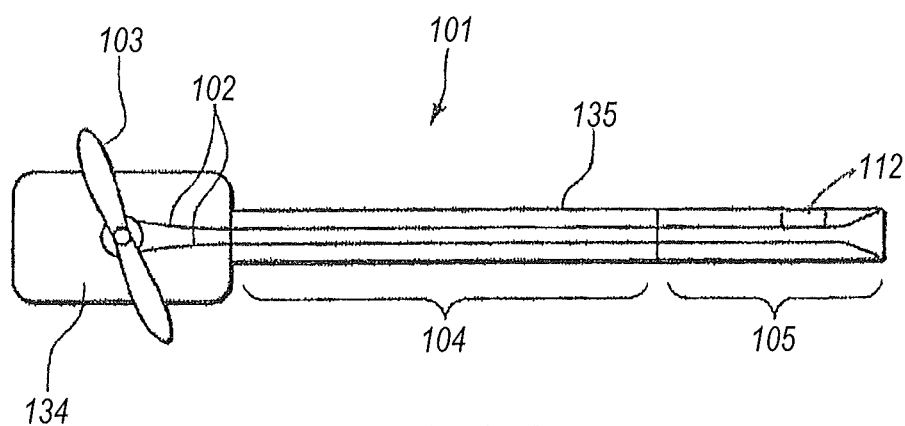
FIG. 16A illustrates an example of an elongate instrument such as a conventional manually operated catheter.
Figure 16B:
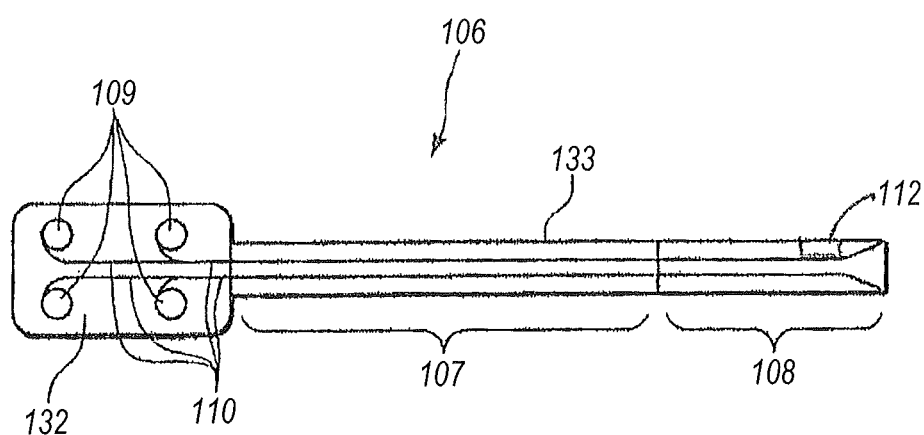
FIG. 16B illustrates another example of an elongate instrument such as a robotically-driven steerable catheter.

FIG. 1 shows one variation of a localization system. A typical operation room set up including a bed 1, a fluoroscopy system 2 and an electromagnetic field generator 4 positioned next to the bed 1 for tracking or detecting the location of a localization sensor 6 is shown. The localization sensor coordinate system (S) is fixed to the sensor 6 to provide the location, position and/or orientation of the sensor 6. The sensor 6 may be coupled to an elongate instrument. The elongate instrument is not shown in FIG. 1, but examples of elongate instruments having a sensor coupled thereto, which may be used in the system of FIG. 1 or the systems illustrated in any of the other figures described herein are shown in FIGS. 16A-16B. The electromagnetic field generator coordinate system (T) is attached to the electromagnetic field generator 4. The location of the localization sensor 6, e.g., its position and/or orientation, may be measured in the coordinate system of the field generator. The reference coordinate system (R) is an alternative coordinate system attached to the reference sensor 7. It is possible, and sometimes it may be more desirable, to locate and measure the localization sensor 6 in the reference sensor coordinate system (R). The fluoroscopy coordinate system (F) is attached to an image intensifier 8, e.g., in the middle of the image intensifier. The model coordinate system (M) is the coordinate system used for describing the 3D model 9 or image (shown in display 10).

With reference to the exemplary localization system, including the coordinate systems or frames described above, various registration processes or techniques are described herein.

In certain variations, localization data can be registered to a 3D anatomical model or a fluoroscopy image. The techniques used to perform the registration vary depending on the target. Where localization data is registered to a fluoroscopy image, the 2D nature of the fluoroscopy images may require that multiple images be taken at different angles before the registration process is complete. A marker that shows up in both or multiple images may be provided or required. A convenient choice is to embed a fluoro marker in the patient table so that the marker is visible in all fluoro images, effectively using it as the reference sensor. Once the marker is located in multiple images, its 3D position is easily identified via triangulation. Where localization data is registered to a 3D anatomical model, fiducials or detailed knowledge of a specific spot or point in the 3D model, e.g., its location, position and/or orientation, may be required. A patient reference patch may simplify the registration process. Since the 3D model is acquired during a pre-op CT scan, a patient reference patch worn during the scan provides the reference point for future registration. The patch is in essence a location sensor that also shows up in the CT scan. Because the patch provides its current position and orientation, there is enough information to align the 3D anatomical model to the patient during live cases once the patch is identified in the 3D model.

In addition, the patient reference patch may not be needed if the catheter is registered to a particular anatomical feature. The idea is to embed markers in the catheter and drive the catheter to the particular anatomical structure under the guidance of fluoro. A predefined section of the 3D model representing the anatomical structure is then registered to the catheter once the physician clicks through the markers to recognize their 3D location. In another variation of this approach, the 3D model is marked instead with a few easy-to-reach target locations. As before, the physician drives the catheter to those locations in succession under fluoro, and registers the position and orientation of the catheter each time it reaches a target. After collecting a few data points, the 3D model can be registered to the catheter for use in live cases.

Whether registering localization data to a 3D anatomical model or a fluoroscopy image, in certain variations, a reference sensor may be utilized and may greatly simplify the registration process. While a localization sensor may be measured or tracked in the Traxtal or electromagnetic field generator coordinate frame, the Traxtal system may be sensitive to the presence of metal in or nearby its electromagnetic field generator. As such, close proximity of an image intensifier of a fluoroscopy system may have detrimental effects on the workspace of the localization or tracking system. This problem may be alleviated by the introduction of a reference sensor or an extra sensor placed in the workspace of the electromagnetic field generator.

Figure 2A:
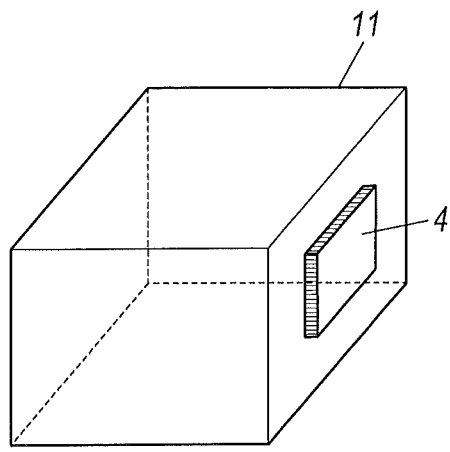
FIG. 2A illustrates a workspace of an electromagnetic field generator without a reference sensor.
Figure 2B:
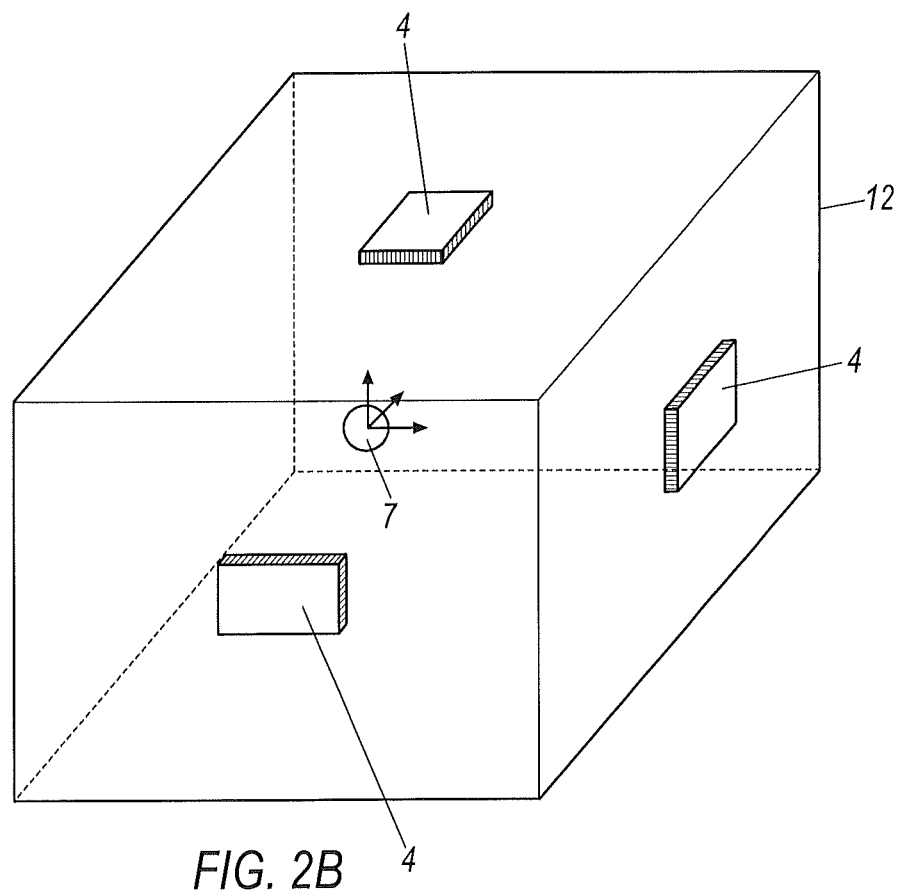
FIG. 2B illustrates an extended workspace of an electromagnetic field generator where a reference sensor is utilized.

FIG. 2A shows a workspace 11 of the electromagnetic field generator 4 without a reference sensor. FIG. 2B shows an extended workspace 12 of the electromagnetic field generator 4 with a reference sensor 7. FIG. 2B shows the electromagnetic field generator 4 positioned in different locations. The electromagnetic field generator 4 can be moved to different locations, thereby expanding the workspace for elongate instrument tracking or localization, due to the presence of the reference sensor 7. The reference sensor 7 sets up a reference coordinate frame or system (R), which provides an alternative coordinate system independent of the placement of the electromagnetic field generator 4. The location, position and/or orientation of a localization sensor may be measured in the reference coordinate frame or system (R) instead of the electromagnetic field generator coordinate frame or system (T), via a transformation. With the reference coordinate system or frame in place, the electromagnetic field generator 4 may be moved around without distorting the measurement of the localization sensor in the reference coordinate frame, effectively extending the workspace 12 of the electromagnetic field generator 4 and the localization or tracking system.

Figure 3A:
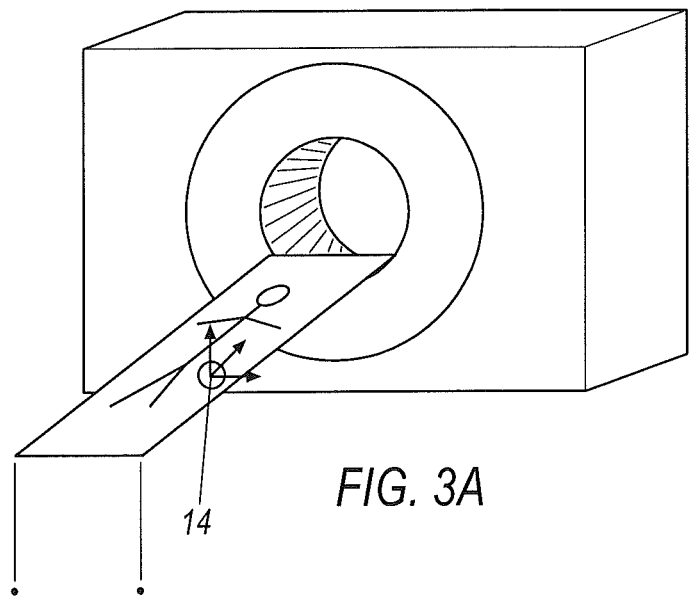
FIG. 3A illustrates a patient wearing a reference sensor anatomy patch as the patient is undergoing a pre-op scan.
Figure 3B:
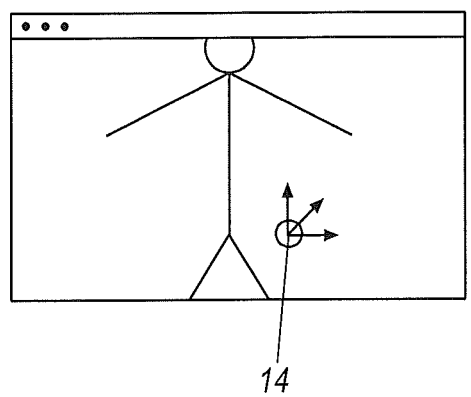
FIG. 3B illustrates a 3D model or image showing both a patient and a reference sensor anatomy patch worn by the patient.

In certain variations, the reference sensor may be used as an anatomy patch 14. As shown in FIGS. 3A and 3B, the reference sensor anatomy patch 14 may be worn by a patient during a pre-op scan so that the anatomy patch 14 appears in the resulting 3D model. As a result, the location, position and/or orientation of the anatomy patch 14 may be described or measured in the model coordinate system or frame (M). Where the reference sensor is used as the anatomy patch 14, the description of the anatomy patch 14 defines the transformation between the reference coordinate frame and the model coordinate frame ($_{M/R}T$). FIGS. 3A and 3B show a reference sensor anatomy patch 14 applied to a patient for registration. FIG. 3A shows a patient wearing an anatomy patch 14 as the patient is undergoing a pre-op scan. FIG. 3B shows a 3D model or image showing both the patient and the anatomy patch 14 in the image.

3D Registration

In certain variations, localization data can be registered to a 3D anatomical model. The 3D registration process aligns the localization sensor measurement or localization data to the 3D model. The required transformations to complete the registration may differ slightly depending on whether a reference sensor is used in the localization sensor measurement or not.

Figure 4A:
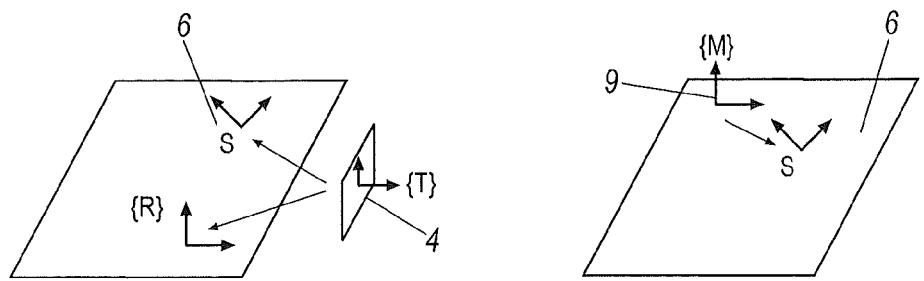
FIG. 4A describes a transformation for registering localization data or measurements from an electromagnetic localization sensor to a 3D model.

FIG. 4A describes a transformation for registering localization data or measurements from an electromagnetic localization sensor to a 3D model, where a location of the localization sensor 6 is measured in the Traxtal electromagnetic field generator 4 coordinate system (T). One example of a transformation $_{M/T}T$ required to describe the localization sensor measurement from the Traxtal electromagnetic field generator coordinate system (T) in the 3D model 9 coordinate system (M) is shown in FIG. 4A.

Figure 4B:
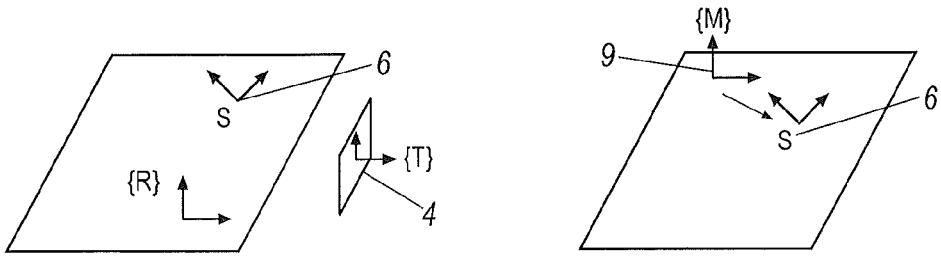
FIG. 4B describes another transformation for registering localization data or measurements from an electromagnetic localization sensor to a 3D model.

FIG. 4B describes the transformation for registering localization data or measurements from an electromagnetic localization sensor to a 3D model, where a location of the localization sensor 6 is measured in the reference sensor 7 coordinate system (R). One example of a transformation $_{M/R}T$ required to describe the localization sensor measurement from the reference sensor coordinate system (T) in the 3D model 9 coordinate system (M) is shown in FIG. 4B. The transformation $_{M/R}T$ is simpler than the transformation $_{M/T}T$. The transformation $_{M/R}T$ may not require any online computation. The transformation $_{M/R}T$ may be fixed in space and does not need to be computed again.

In a variation where the reference sensor doubles as an anatomy patch as described above, transformation $_{M/R}T$ may be computed offline once the model is acquired. The localization sensor location in the model coordinate system may then be calculated from:

$$^Mp_S = {_R^M}T {^Rp_S}$$

Where $^Mp_S$ and $^Rp_S$ are position vectors to the localization sensor described in the model coordinate system and in the reference coordinate system.

Fluoro Registration

Figure 5:
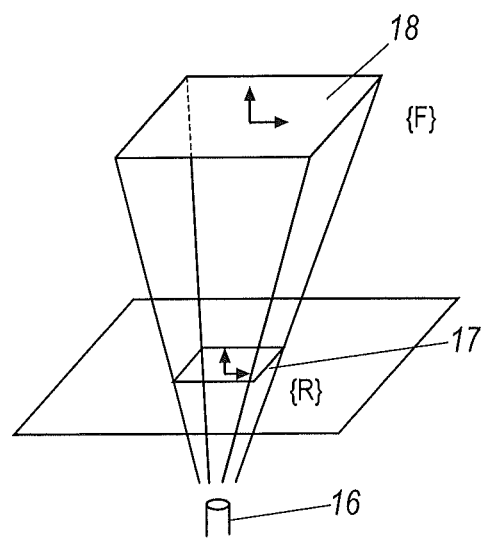
FIG. 5 illustrates a projection process required to generate an image from an object placed in between an x-ray source and an image intensifier.

In certain variations, localization data can be registered to a fluoroscopy image. The fluoro registration process may align the localization sensor measurement or localization data (e.g., from a Traxtal system or electromagnetic sensor) to a 2D fluoroscopy image. FIG. 5 shows a projection process required to generate an image from a 3D object or other object placed in between a source or x-ray source 16 and an image intensifier 18. The ray coming out of the x-ray source 16 goes through the object and reaches the image intensifier 18 to produce a fluoroscopy image. As such, a fluoro registration process may be closely related to the process of projecting the localization data onto the x-y plane of the fluoroscopy coordinate system. FIG. 5 also shows a reference sensor 17 having a reference coordinate frame (R). A projection matrix may be used to transform the reference coordinate system (R) to the fluoroscopy coordinate system (F).

Information about the imaging system may be required to perform the fluoro registration process. The information or parameters of interest may include: the size of the image intensifier; the distance from the x-ray source to the image intensifier; the distance from the x-ray source to the bed; and the axis of rotation if the fluoro imaging system or C-arm is to be rotated. A preliminary calibration step may be necessary to obtain such information unless it is readily provided by the manufacturer of the imaging system.

The physical dimension of the image intensifier helps determine the scale factor, which provides a mapping from pixels to millimeters. It is computed from comparing the size of the image intensifier to that of the window showing the fluoro image so that 1 pixel difference in the fluoro image corresponds to the correct length in millimeters in the real world.

Figure 6:
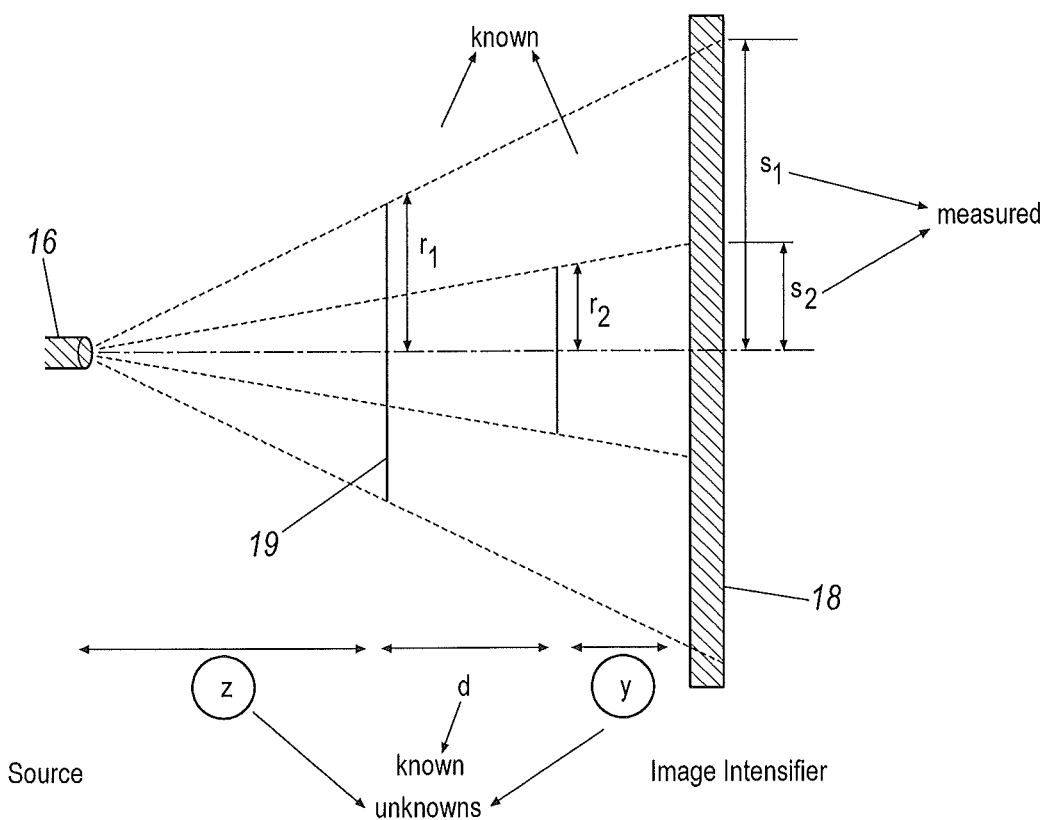
FIG. 6 shows a variation of how to estimate or determine the distances from the x-ray source to the bed and to the image intensifier.

Knowing the distances is important in setting up a correct projection. FIG. 6 describes a variation of how to estimate or determine (fluoro calibration) the distances from the x-ray source 16 to the bed 19 and to the image intensifier 18 using an object of known dimensions. FIG. 6 shows a side view of the system where the bed 19 is at x away from the source 16 and the image intensifier 18 is at y away from the source 16. To calculate the unknowns x and y, imagine there are two disks of known radii, $r_1$ and $r_2$, stacked up together with known distance of separation, d. The radii of the disks appearing on the fluoro image are measured as $s_1$ and $s_2$, respectively. The relationship among the variables are described by the following equations:

$$\frac{r_1}{x} = \frac{s_1}{x+d+y}$$

$$\frac{r_2}{x+d} = \frac{s_2}{x+d+y}$$

which leads to the expression for calculating the unknowns x and y:

$$\begin{pmatrix} r_1 - s_1 & r_1 \\ r_2 - s_2 & r_2 \end{pmatrix} \begin{pmatrix} x \\ y \end{pmatrix} = \begin{pmatrix} -r_1 d \\ -r_2 d + s_2 d \end{pmatrix}$$

Figure 7:
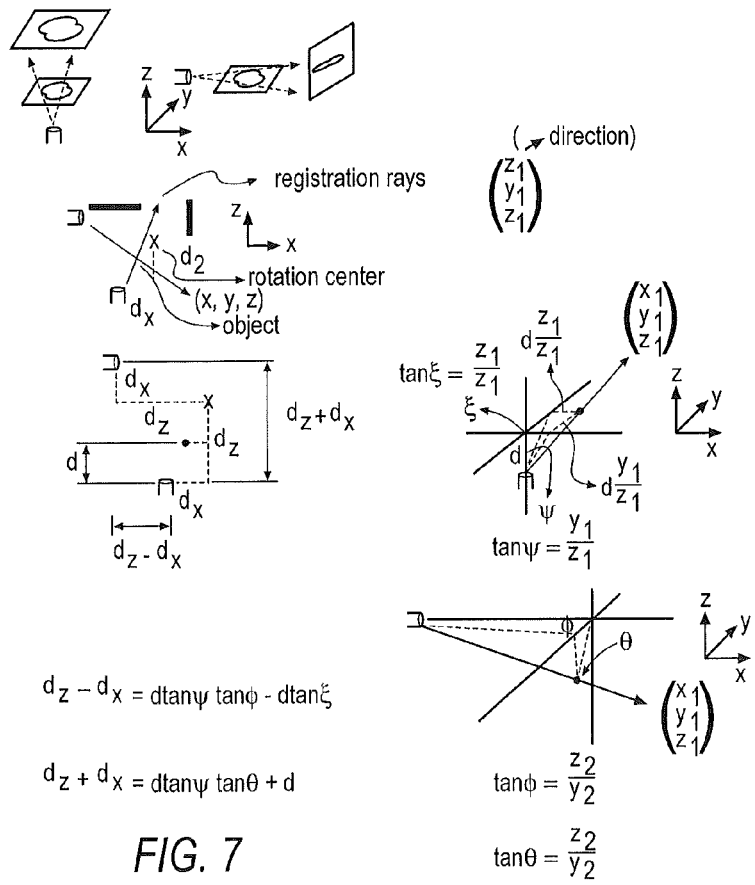
FIG. 7 shows a variation for determining or estimating the axis of rotation by searching for its offsets from a source.
Figure 8:
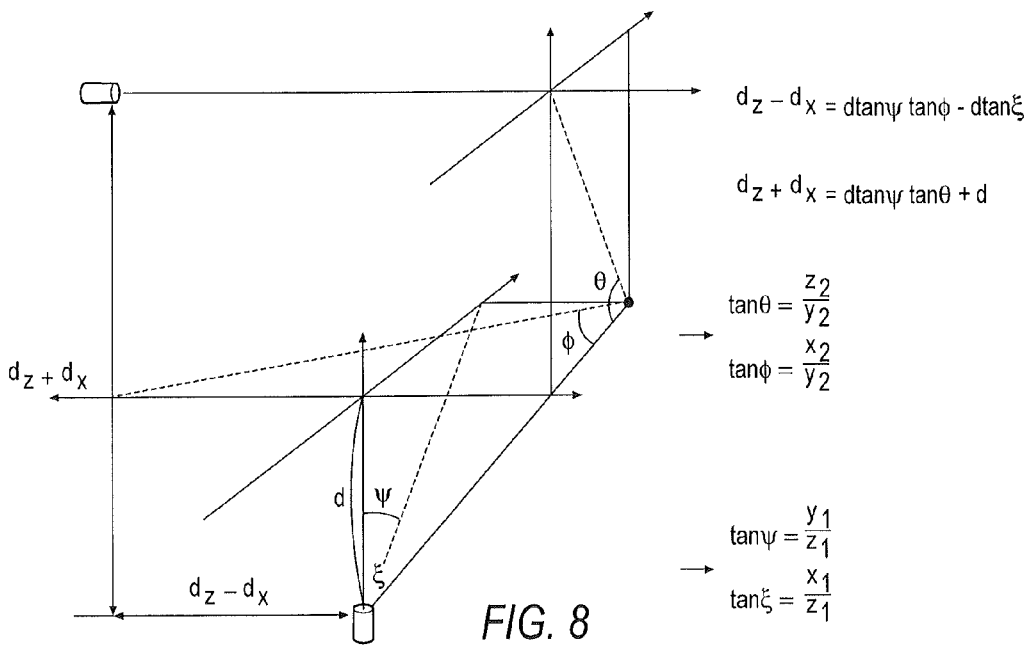
FIG. 8 shows another variation for determining or estimating the axis of rotation by searching for its offsets from a source.

In certain variations, the fluoro image may be taken at an oblique angle, which may require the C-arm of the fluoroscopy image to be rotated. However, the x-ray source and the image intensifier are not always perfectly lined up with the axis of rotation, which may remain to be found. FIGS. 7 and 8 describe various ways of determining or estimating the axis of rotation by searching for its offsets from a source. $d_x$ and $d_z$ represent the offsets along the x and z axes, respectively, and d denotes the distance from the source to an object, which can be placed on the bed to take advantage of the known distance to the bed.

The calibration process starts with locating the object in the AP view and then in the LA view. Basically, this process identifies a direction vector from the source to the object of interest in two different set ups. Angles ψ and ξ are defined from the AP view as:

$$\tan(\psi) = \frac{\bar{y}_1}{\bar{z}_1}$$

$$\tan(\xi) = \frac{\bar{x}_1}{\bar{z}_1}$$

and φ and θ are defined from the LA view as $$\tan(\phi) = \frac{\bar{x}_2}{\bar{y}_2}$$

$$\tan(\theta) = \frac{\bar{z}_2}{\bar{y}_2}$$

where $x_1$ are $x_2$ are the x component of the direction vectors toward the object in the AP and LA views. From the geometry, the offset dx and dz are found from the following equations:

$$d_z - d_x = d\,\tan(\psi)\tan(\phi) - d\,\tan(\xi)l$$

$$d_z + d_x = d\,\tan\,d(\psi)\tan(\theta) + d\,\ldots$$

Alternatively, Rodrigues' formula, widely used in kinematics and robotics, may provide a convenient and robust method to locate the axis of rotation.

$$s_{O_n} = \frac{1}{2}\left(p_1 + p_2 + \frac{s \times (p_2 - p_1)}{\tan\left(\frac{\alpha}{2}\right)} - (s(p_1 + p_2))s\right)$$

where $S_{on}$ is the point of interest on the axis of rotation normal to the origin of the global coordinate system, $p_1$ and $p_2$ are the locations of the object in the fluoro coordinate system in LA and AP views, s is the unit vector along the axis of rotation, and α is the degree of rotation. In this case, s is $(0, 1, 0)^T$ and α is π/2.

Figure 9:
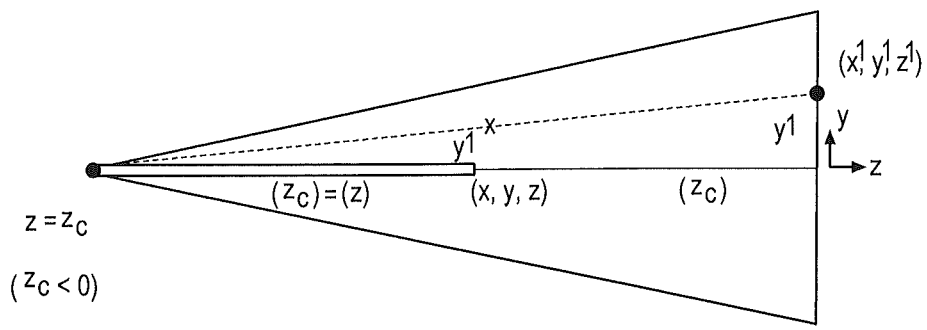
FIG. 9 shows a perspective projection mechanism, which shows how a fluoro image may be acquired.

Once all the variables are determined, the mapping to the fluoro coordinate system (F) may be established. A perspective projection mechanism (from a source to an image intensifier) is described in FIG. 9, showing how the fluoro images may be acquired. The vantage point coincides with the source placed at $z = -z_s$, and yields the transformation matrix in the following Equation $$\begin{pmatrix} x' \\ y' \\ z' \\ w' \end{pmatrix} = \begin{pmatrix} 1 & 0 & 0 & 0 \\ 0 & 1 & 0 & 0 \\ 0 & 0 & 0 & 0 \\ 0 & 0 & -\frac{1}{z_s} & 1 \end{pmatrix} \begin{pmatrix} x \\ y \\ z \\ w \end{pmatrix}$$

which projects a 3D point onto the x-y plane of the fluoro coordinate system (F) after perspective divide, i.e., Fx=x'/y', Fy=y'/w', and Fz=0; or divide x', y' by w' to obtain new coordinates in the fluoro coordinate system.

In order to use the above perspective projection, the localization data should be represented in the fluoro coordinate system. The transformation $_{F/R}T$ is generated when the reference sensor is located in multiple fluoro images taken at different angles. The AP view, i.e., the top view, and the LA view, i.e., the side view, may be utilized to register the sensor location.

Alternatively, fluoro registration may be performed using a single image. A transformation may be generated with a single fluoro image. This would involve use of another sensor, e.g., a sensor 20 being fixed to the bed, which would provide the bed coordinate system (B). A bed sensor and/or reference sensor may be fixed or have a known location. This single image fluoro registration process computes a transformation between the fluoro coordinate system (F) and the bed coordinate system (B), i.e., $_{F/B}T$ and then uses $_{B/R}T$ to get the desired transformation $_{F/R}T$. $_{B/R}T$ is computed by taking the difference between the two sensor readings, i.e. the relative measurement between the bed 20 and the reference 21 sensors. The idea is to use a sensor instead of a fluoro marker to locate the bed in 3D space. The use of a bed sensor provides a couple of key advantages: frame transformation between the bed and the reference sensor, and robustness to table tilting. As noted before, it is possible to figure out the exact location of the bed sensor in fluoro coordinate system once distances among the source, the bed and the image intensifier are discovered. What is different this time is that the bed sensor provides a relative transformation to the reference sensor because both are measured in the same Traxtal or other sensor coordinate system. This facilitates the computation of reference sensor position and orientation in fluoro coordinate system, which is what is desired. In addition, the bed sensor provides orientation information as well as position data. Bed sensor measurement in the fluoro coordinate system is robust to table tilting because the measurement already reflects the change in table orientation. This allows the physician to reposition or reorient the patient as need arises in the tightly spaced operating room. The process for single image registration is similar to normal fluoro registration that requires fluoro images taken at multiple angles, except that there is no need to rotate the fluoro C-arm and thus saves preparation time and operating room space significantly. In summary, first perform normal fluoro registration process to identify various dimensions of the fluoro machine, such as distances between crucial pieces. Once the variables are known, make sure the bed sensor shows up in the fluoro view. Finally, locate the bed sensor in the fluoro view and click on it or select it to recognize its location on the screen, and the process is completed.

Figure 10A:
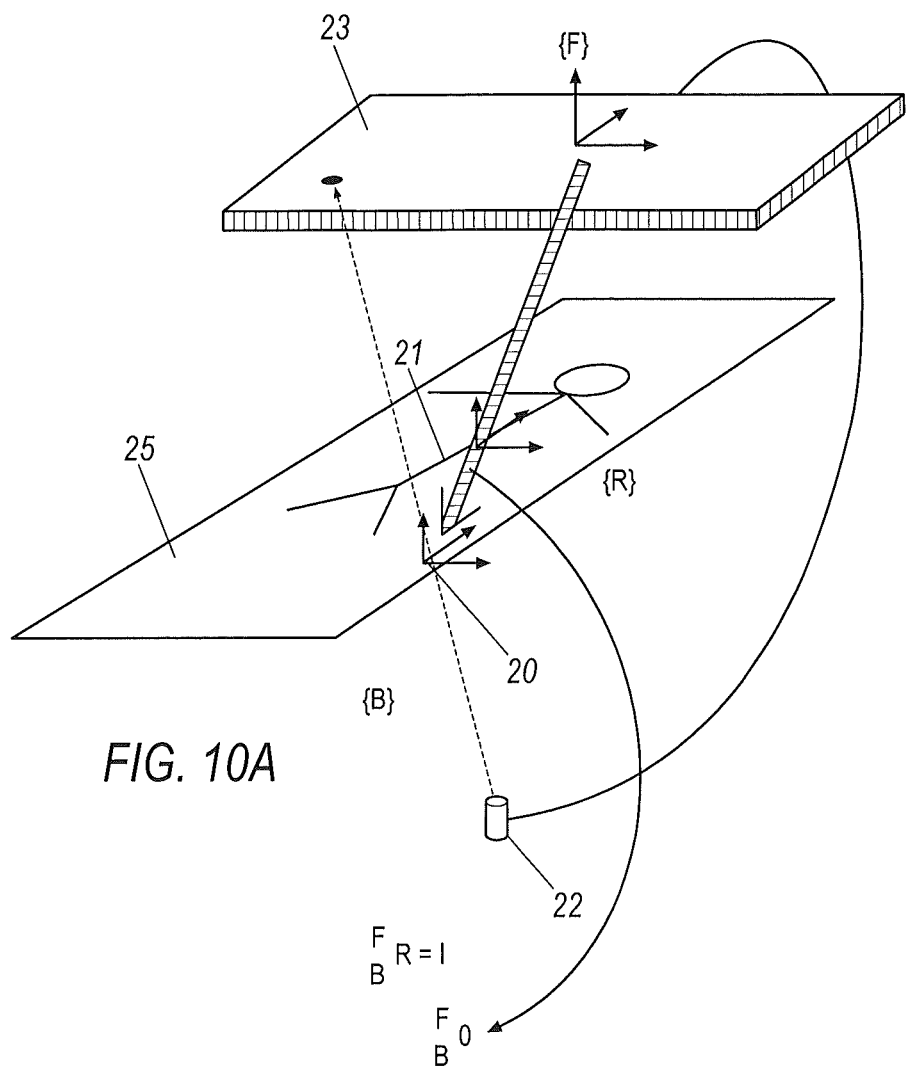
FIG. 10A shows a technique for performing fluoro registration using a single image.
Figure 10B:
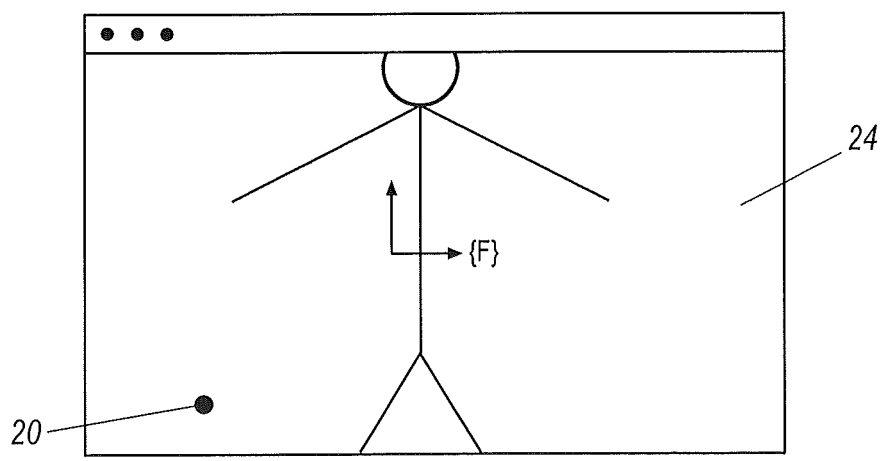
FIG. 10B shows a fluoro image having a bed sensor visible therein, for performing fluoro registration using a single image.

In order to get $_{F/B}T$, the operator locates the bed sensor 20 in the fluoro image 24 (FIG. 10B) to generate an imaginative ray stemming from the source 22 that goes through the bed sensor 20 as shown in FIG. 10A. The exact location of the bed sensor 20 is then determined using the knowledge of the source 22 to the image intensifier 23 distance and the height of the bed 25, and then the translation of the origin $_{F/B}O$ is calculated from taking the difference in position between (F) and (B).

In addition or in the alternative, the bed sensor 20 may be installed to have the identical orientation as the fluoro coordinate system to simplify the transformation, i.e., $_{F/B}R=I$. The resulting transformation is:

$$_R^FT=_B^FT_R^BT$$

which takes a measurement in the reference coordinate system, $^Rp_S$, and converts it into the fluoro coordinate system, $^Fp_S$. Then, applying the perspective projection mentioned above will correctly project the measurement $^Fp_S$, onto the x-y plane of the fluoro coordinate system.

Sterile Integration of Localization Systems

Various options for integrating an outside localization or tracking system with a surgical system or robotically controlled instrument, surgical system or elongate instrument, e.g., Hansen's VCCS system, are described herein. For example, an electromagnetic localization sensor or Traxtal system may be integrated with a Hansen robotically controlled elongate instrument or catheter. It is contemplated that various localization systems may be integrated with a robotically controlled elongate instrument or surgical system, e.g., electromagnetic sensor based systems, Traxtal systems, and fiber optic based localization systems. Various localization sensors may be used in any of the integrated systems described below, e.g., electromagnetic sensors, fiber optic sensors, etc.

In certain variations, a medical system for controlling an elongate instrument may include a robotically controlled instrument assembly having a shapeable elongate instrument. A localization system may be coupled to the robotically controlled instrument assembly and configured to track the shapeable elongate instrument, wherein at least a portion of the localization system may be sterilely isolated from the robotically controlled instrument assembly.

Figure 11:
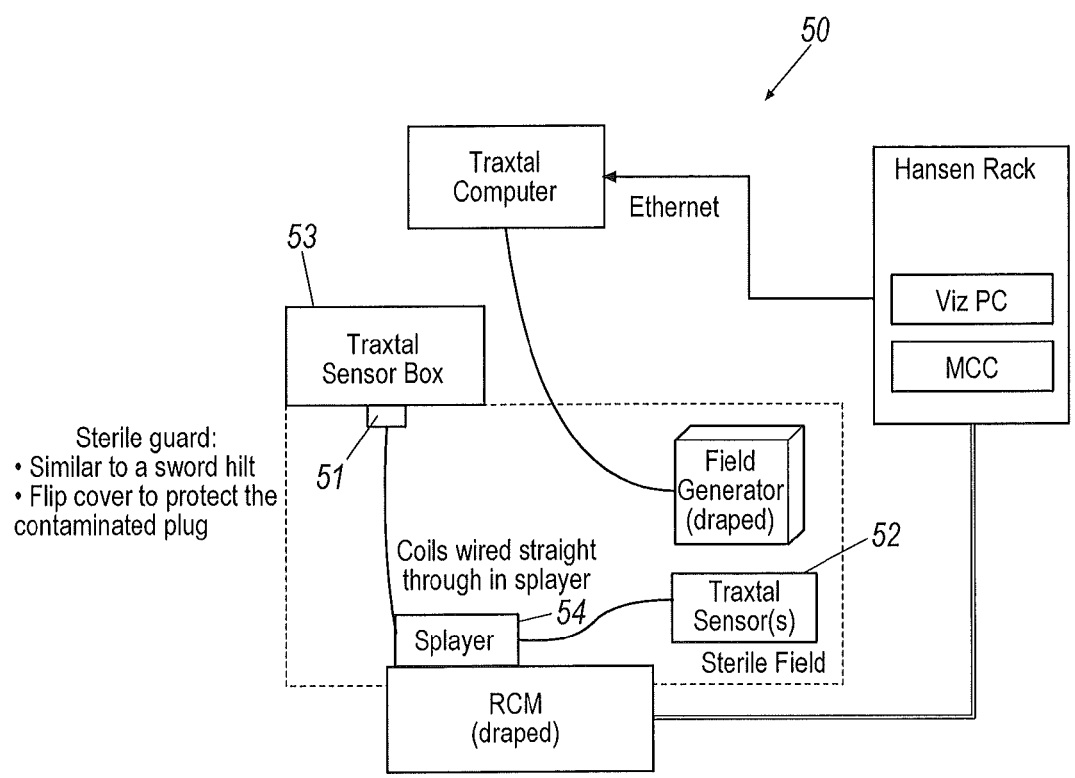
FIG. 11 illustrates a variation of a localization system integrated with a robotically controlled instrument or surgical system.

FIG. 11 shows one example of a medical system 50 for controlling an elongate instrument. The system 50 may include an integrated localization system. The localization system may include a localization sensor 52 coupled to a shapeable elongate instrument within a sterile field. The localization sensor 52 may be coupled to a sensor detection unit 53 positioned outside of the sterile field via a connector 51. The connector 51 may be positioned within the sterile field. Optionally, the connector 51 may be positioned outside of the sterile field.

As shown in FIG. 11, coil lead wires may be directly soldered to a cable inside of the robotically controlled instrument assembly or splayer 54, and then routed to the standard connector 51 connected to the sensor box or sensor detection unit 53. A sterile guard may be implemented on the connector 51 to produce the following workflow: 1. The connector 51 may be unplugged by a sterile assistant with isolation from the contaminated plug; 2. A flip cover or sterile guard my protect the contaminated plug; and 3. The assembly of wires and/or connector, now sterile, can be placed in the sterile field, e.g., on a tray, when the catheter or elongate instrument is removed.

Figure 12:
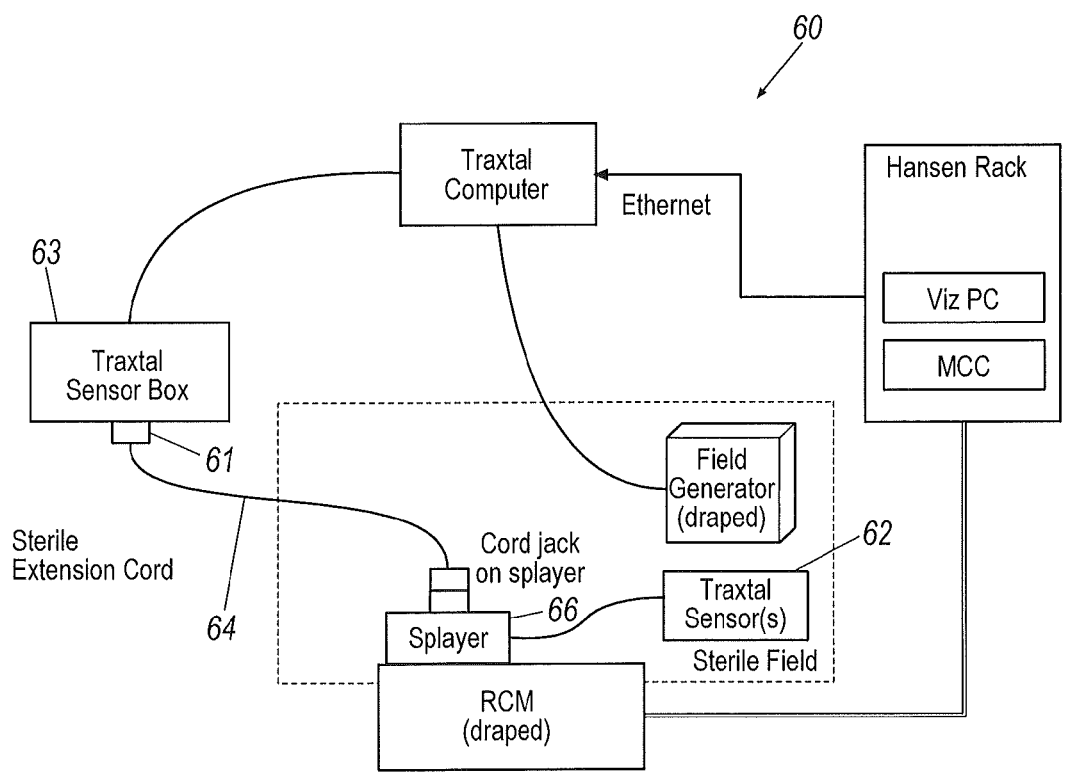
FIG. 12 illustrates a variation of a localization system integrated with a robotically controlled instrument or surgical system.

FIG. 12 shows another example of a medical system 60 for controlling an elongate instrument. The system 60 may include an integrated localization system. The localization system may include a localization sensor 62 coupled to the shapeable elongate instrument within a sterile field. The localization sensor 62 may be coupled to a sensor detection unit 63 positioned outside of the sterile field via an extension cord or wire 64 and a connector 61. At least a portion of the wire 64 may be positioned in the sterile field and the connector 61 may be positioned outside of the sterile field. Optionally, a second connector 65 for coupling the localization sensor to the sensor detection unit may be included. The second connector 65 may be positioned within the sterile field. The second connector 65 may be robust or resistant to bodily fluids.

As shown in FIG. 12, a sterile cord or wire 64 (e.g., standard length) may connect through a drape to a jack on the robotically controlled instrument assembly or splayer 66, which is internally wired to lead wires of the sensor coils. The disconnection procedure for this system may be as follows: 1. Remove the plug or connector 65 from the splayer jack; 2. Lay the plug and cord 64 on the table (still in the sterile field); and 3. Remove the full catheter or elongate instrument. Since the sterile end of the cord 64 stays in the sterile field, there is no contamination on reconnection. Also, there is no unwieldy cable that needs to be managed. In certain variations, the sensor box or sensor detection unit may be integrated into the computer (e.g., a Traxtal sensor box may be integrated into a Traxtal computer) to reduce the number of items at a bedside.

Figure 13:
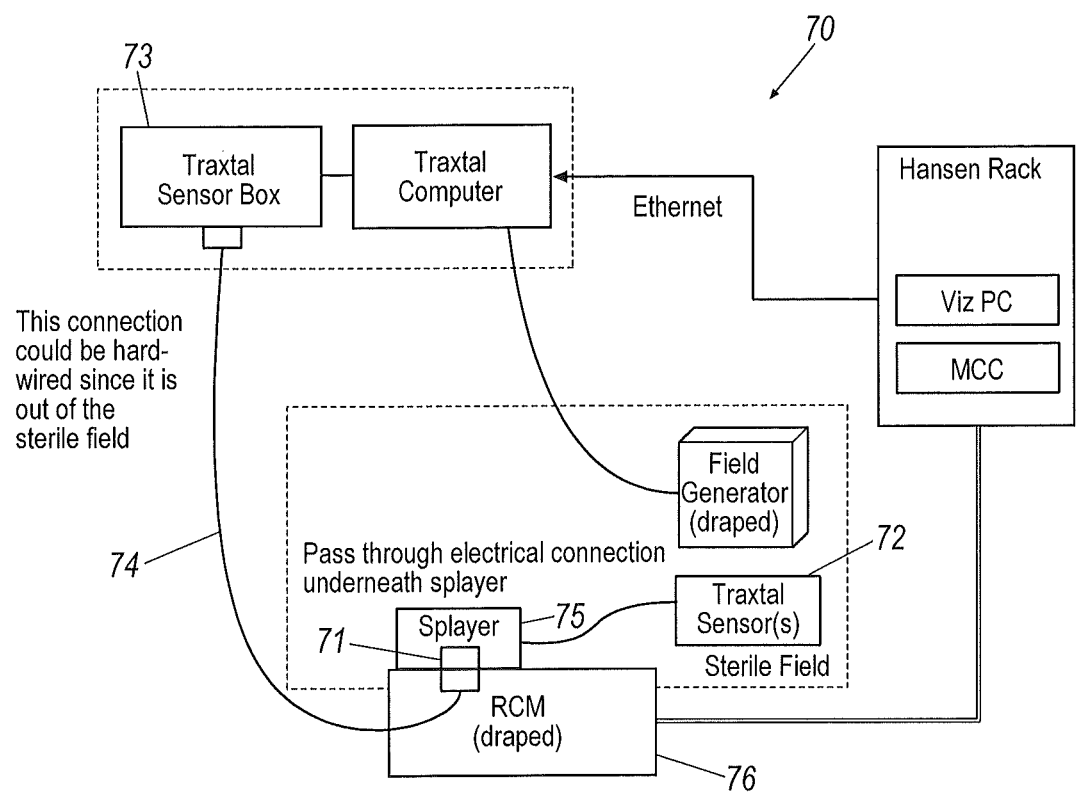
FIG. 13 illustrates a variation of a localization system integrated with a robotically controlled instrument or surgical system.

FIG. 13 shows another example of a medical system 70 for controlling an elongate instrument. The system 70 may include an integrated localization system. The localization system may include a localization sensor 72 coupled to the shapeable elongate instrument within a sterile field. The localization sensor 72 may be coupled to a sensor detection unit 73 positioned outside of the sterile field via a cord or wire 74 and a connector 71. The entire or substantially all of the wire 74 may be positioned outside of the sterile field.

Figure 14:
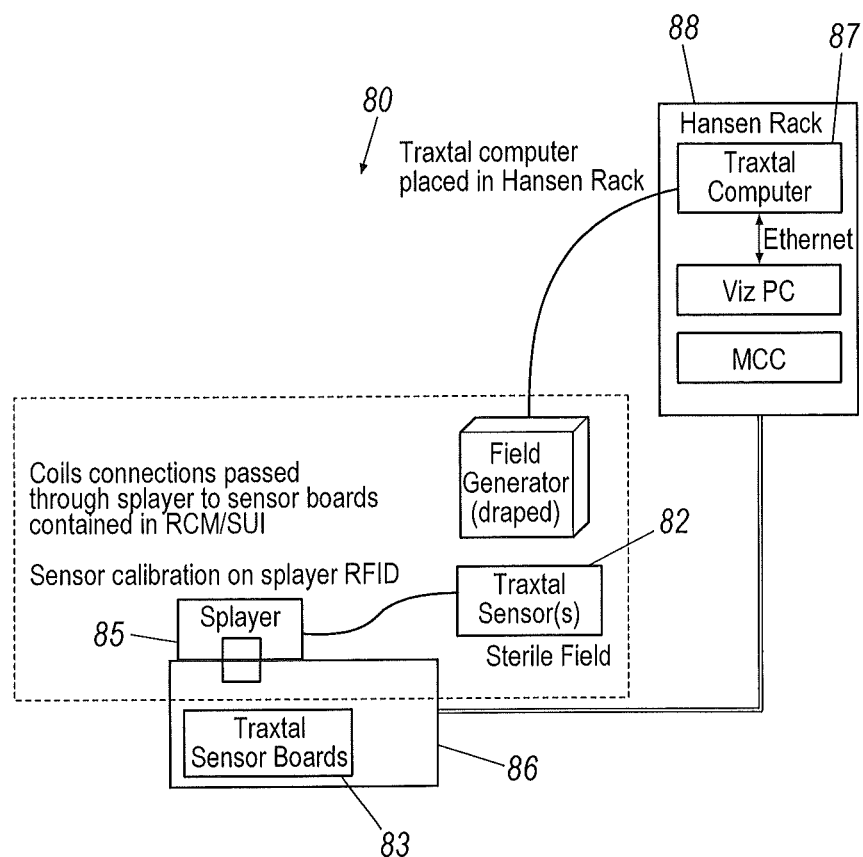
FIG. 14 illustrates a variation of a localization system integrated with a robotically controlled instrument or surgical system.
Figure 15:
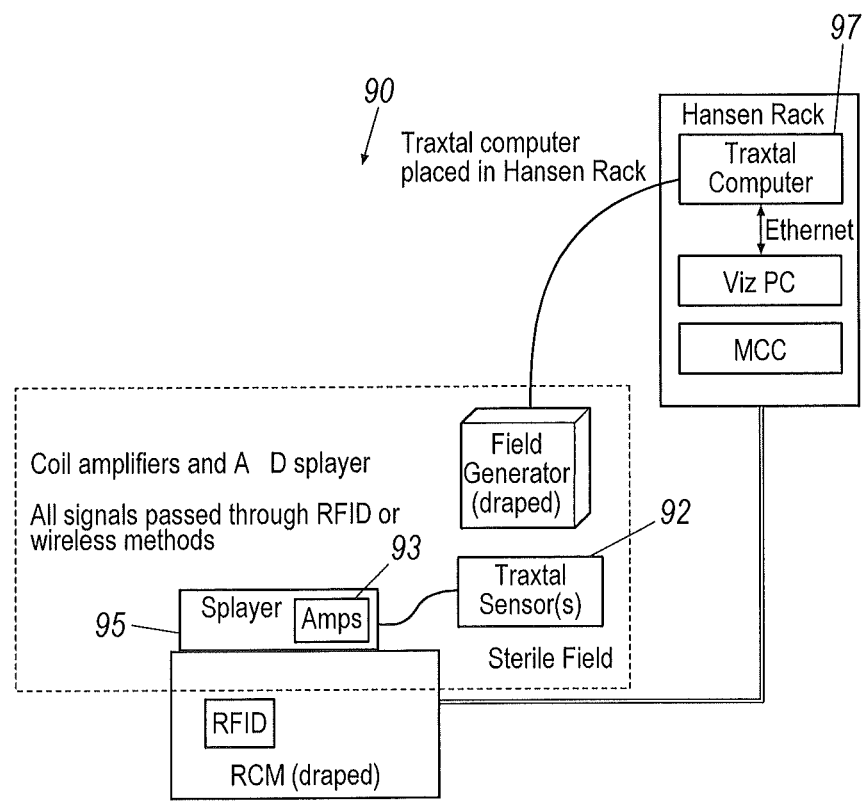
FIG. 15 illustrates a variation of a localization system integrated with a robotically controlled instrument or surgical system.

As shown in FIG. 13, instead of using an extension cord jacked into the robotically controlled instrument assembly or splayer 75, a connector 71 may be implemented under the robotically controlled instrument assembly or splayer 75, routed through an instrument driver 76 or RCM and then out to the sensor box 73 or sensor detection unit or a bedside box, e.g., a Traxtal bedside box including both a Traxtal sensor box and a Traxtal computer. An advantage of this variation is that none of the cabling is within the sterile field since it is routed through the drape and into the instrument driver or RCM FIG. 14 shows another example of a medical system 80 for controlling an elongate instrument. The system 80 may include an integrated localization system. The localization system may include a localization sensor 82 coupled to the shapeable elongate instrument within a sterile field. The localization sensor 82 may be coupled to a sensor detection unit 83. The sensor detection unit 83 may be integrated into an instrument driver 86 coupled to a robotically controlled instrument assembly 85 or splayer. The sensor detection unit 83 may communicate via a digital signal with a sensor controller 87 positioned outside of the sterile field. As shown in FIG. 14, the sensor detection unit 83 or sensor amplifier boards, e.g., Traxtal amplifier boards, may be placed into the instrument driver 86 or RCM, allowing digital signals to be routed to a sensor controller 87 or Traxtal computer positioned outside of the sterile field, e.g., located in a Hansen rack 88, which may include visualization/robot control computers, router to manage communication between computers, and/or power electronics).

In certain variations, where an electromagnetic field generator of the localization system is positioned in a rack, a small electromagnetic field generator box, which converts an analog signal into a digital signal to drive the sensor coils, may be utilized. Alternatively, an addition to a field generator may be made to avoid analog transfer of information. Optionally, the electromagnetic field generator box may be placed in the RCM or instrument driver.

FIG. 14 shows another example of a medical system 90 for controlling an elongate instrument. The system 90 may include an integrated localization system. The localization system may include a localization sensor 92 coupled to the shapeable elongate instrument within a sterile field. The localization sensor 92 may be coupled to a sensor detection unit 93. The sensor detection unit 93 or amplifier may be integrated in the robotically controlled instrument assembly 95 and the sensor detection unit 93 may wirelessly communicate, e.g., via RFID, with a sensor controller 97 positioned outside of the sterile field. As shown in FIG. 14, an amplifier or sensor detection unit 93 may be placed into the robotically controlled instrument assembly or splayer 95 and transmit signals wirelessly. This would provide a no wire splayer interface.

In any of the variations described herein, the robotically controlled instrument assembly may be disposable. Various localization sensors may be used in any of the systems described herein, including electromagnetic localization sensors or fiber optic sensors. The various methods and system described herein may provide real time visualization of the movement or location of an elongate instrument or other medical instrument while avoiding or minimizing exposing a patient to excessive radiation. Alternatively, any of the medical systems, localization systems or tracking systems described herein may be coupled by wires and/or may be coupled wirelessly.

Exemplary elongate instruments for use in any of the localization or tracking systems described herein are illustrated in FIGS. 16A and 16B. Referring to FIG. 16A, a conventional manually-steerable catheter (101) is depicted. Pullwires (102) may be selectively tensioned through manipulation of a handle (103) on the proximal portion of the catheter structure to make a more flexible distal portion (105) of the catheter bend or steer controllably. The handle (103) may be coupled, rotatably or slidably, for example, to a proximal catheter structure (134) which may be configured to be held in the hand, and may be coupled to the elongate portion (135) of the catheter (101). A more proximal, and conventionally less steerable, portion (104) of the catheter may be configured to be compliant to loads from surrounding tissues (for example, to facilitate passing the catheter, including portions of the proximal portion, through tortuous pathways such as those formed by the blood vessels), yet less steerable as compared with the distal portion (105).

Referring to FIG. 16B, a robotically-driven steerable catheter (106), has some similarities with the manually-steerable catheter (101) of FIG. 16A in that it has pullwires or other control elements (101) associated distally with a more flexible section (108) configured to steer or bend when the control elements (110) are tensioned in various configurations, as compared with a less steerable proximal portion (107) configured to be stiffer and more resistant to bending or steering. The control elements can be flexible tendons, or other mechanical structures that allow for steering or deflection of the catheter (106). The depicted embodiment of the robotically-driven steerable catheter (106) comprises proximal axles or spindles (109) configured to primarily interface not with fingers or the hand, but with an electromechanical instrument driver configured to coordinate and drive, with the help of a computer, each of the spindles (109) to produce precise steering or bending movement of the catheter (106). The spindles (109) may be rotatably coupled to a proximal catheter structure (132) which may be configured to mount to an electromechanical instrument driver apparatus, such as that described in the U.S. patent application Ser. No. 11/176,598, and may be coupled to the elongate portion (133) of the catheter (106).

Each of the variations of elongate instrument depicted in FIGS. 16A and 16B may include a localization sensor 112 coupled thereto as described herein. The localization sensor may be positioned at the distal end or distal portion of the elongate instrument or along a length of the elongate instrument. Various localization sensors may be utilized such as electromagnetic sensors, fiber optic sensors, and other sensors known in the art. Each of the variations depicted in FIGS. 16A and 16B may have a working lumen (not shown) located, for example, down the central axis of the catheter body, or may be without such a working lumen. If a working lumen is formed by the catheter structure, it may extend directly out the distal end of the catheter, or may be capped or blocked by the distal tip of the catheter. It is highly useful in many procedures to have precise information regarding the position of the distal tip or other portion of such catheters or other elongate instruments, such as those available from suppliers such as the Ethicon Endosurgery division of Johnson & Johnson, or Intuitive Surgical Corporation. The examples and illustrations that follow are made in reference to a robotically-steerable catheter such as that depicted in FIG. 16B, but as would be apparent to one skilled in the art, the same principles may be applied to other elongate instruments, such as other elongate instruments, highly flexible or not, from suppliers such as the Ethicon Endosurgery division of Johnson & Johnson, Inc., or Intuitive Surgical, Inc.

In certain variations, a method of controlling a robotically controlled elongate instrument in real time may include one or more of the following steps: displaying an image of an anatomy of a patient; tracking or detecting a localization sensor coupled to the robotically controlled elongate instrument; and registering localization data from the localization sensor to the image to provide a continuously updated location of at least a portion of the elongate instrument in the image of the anatomy of a patient to facilitate robotic navigation of the elongate instrument through the anatomy.

In certain variations, a system for tracking or localizing a robotically controlled elongate instrument may include: an image of an anatomy of a patient; an electromagnetic localization sensor coupled to an elongate instrument; and/or an electromagnetic field generator. The generator may be configured to produce an electromagnetic field in which the electromagnetic localization sensor is detected. The localization sensor may provide localization data for at least a portion of the elongate instrument, where the localization data may be registered to the image to provide a continuously updated location of at least a portion of the elongate instrument in the image. This may facilitate robotic navigation of the elongate instrument through the anatomy.

In certain variations, a system for tracking or localizing a robotically controlled elongate instrument may include: an image of an anatomy of a patient; an electromagnetic localization sensor coupled to an elongate instrument; an electromagnetic field generator; and/or at least one reference sensor, e.g., fixed reference sensor, positioned in a workspace of the electromagnetic field generator. The electromagnetic field generator may be movable relative to the reference sensor thereby expanding the workspace for elongate instrument tracking.

In certain variations, a method of tracking or localizing a robotically controlled elongate instrument in real time may include one or more of the following steps: displaying a single image of an anatomy of a patient; tracking or detecting a localization sensor coupled to the robotically controlled elongate instrument; and/or registering localization data from the localization sensor to the image via a reference sensor to provide a continuously updated location of at least a portion of the elongate instrument in the image of the anatomy of a patient to facilitate robotic navigation of the elongate instrument through the anatomy.

In certain variations, a medical system for controlling an elongate instrument may include a robotically controlled instrument assembly comprising a shapeable elongate instrument. The system may include a localization system coupled to the robotically controlled instrument assembly and configured to track the shapeable elongate instrument, where at least a portion of the localization system is sterilely isolated from the robotically controlled instrument assembly.

In certain variations, a system or robotic system for controlling an elongate instrument with respect to a target space may include an elongate instrument having a localization sensor coupled thereto. The system may include a robotic drive system including at least one actuator, where the robotic drive system is configured to interchangeably couple with the elongate instrument to position the instrument with respect to the target space. The system may also include a controller configured to produce a registration between a localization sensor frame and an image frame or a patient frame. The controller can produce a plurality of signals to direct the robotic drive system or elongate instrument in the image frame using the registration and the image may include an image of the target space or patient.

The localization sensor may be any of various localization sensors, e.g., an electromagnetic localization sensor. An electromagnetic localization sensor may be placed in a pulsating magnetic field generated by an electromagnetic field generator to allow for sensor detection or tracking.

A position and/or orientation of the localization sensor may be continuously tracked to allow for accurate manipulation of the elongate instrument. A variety of images may be utilized, e.g., images generated by CT or 2D or 3D fluoroscopy. For example, the image may be a 3D or 2D anatomical model or a 2D or 3D fluoroscopic image. Registering may include transforming localization data generated by the localization sensor to the coordinate frame of the image such that localization data of the elongate instrument is overlaid on the image.

An image intensifier may be provided, where localization data from the localization sensor may be registered to a fluoroscopy coordinate system of a fluoroscopy image coupled to an image intensifier. Registration to a fluoroscopy image may be produced by knowing: a distance from an X-ray source to the image intensifier, a distance from the source to a bed, a size of the image intensifier, and/or the axis of rotation of a c-arm of a fluoroscopy system. In certain variations, the robotically controlled elongate instrument may be a vascular catheter or other catheter. In certain variations, the registration may be used to facilitate intuitive or instinctive driving of the elongate instrument. A single image or multiple images may be utilized. A master input device may be coupled to the controller, where the master input device uses the registration to permit intuitive or instinctive driving of the elongate instrument using the robotic drive system.

In certain variations, a robotic system for controlling an elongate instrument with respect to a target space may include an elongate instrument having a localization sensor coupled thereto. The system may include a robotic drive system having at least one actuator. The robotic drive system may be configured to interchangeably couple with the elongate instrument to position the instrument with respect to the target space. The system may include a controller configured to register localization data from the localization sensor to an image of an anatomy or to a patient or target space frame to provide a continuously updated location of at least a portion of the elongate instrument in the image. The controller can produce a plurality of signals to direct robotic navigation of the elongate instrument through the anatomy based on the location of at least a portion of the elongate instrument in the image.

The controller may be configured to convert a user input into a plurality of signals based on the registration of a sensor reference frame to the image frame or target space or patient reference frame. A master input device may be coupled to the controller, where the master input device uses the registration to permit intuitive or instinctive driving of the elongate instrument using the robotic drive system.

The various systems and methods described herein may, for example, include or utilize any of the systems or methods illustrated in the figures of the present application.

Tracking an Elongate Instrument with an Active Contour

In certain variations, a system or method for tracking or vision tracking a medical instrument or elongate instrument, e.g., robotically controlled, or at least a portion of the instrument in real time in an image may perform or require one or more of the following steps. One or more of a sequence of points may be identified to initialize an active contour or outline of at least a portion of the elongate instrument. The active contour may correspond to at least a portion of the elongate instrument. The active contour may be updated or modified (e.g., lengthened or shortened) as the elongate instrument moves by performing a pixel intensity or density search, focused pixel intensity or density search, color intensity search or other similar search. For example, the active contour may be updated or modified by searching for a change in pixel density or intensity or a change in brightness in the image, e.g., in a fluoroscopy image or other image. An image-based search, e.g., a template matching search, may be performed along the active contour to track a feature or specific point of interest of the elongate instrument. While the below description refers template matching searches, which are one example of an image-based search, other image-based searches may be performed as an alternative to or in addition to the template matching search. The image-based search may be performed to track the active contour or to track a feature, marker or point of interest of the elongate instrument in order to enhance or confirm the accuracy of the active contour. The image-based search may be performed to track a feature, marker or point of interest of the elongate instrument to ascertain the location of the specific feature, marker or point of interest on the active contour or to track the specific feature, marker or point of interest on the active contour. The image-based search may consist of an image correlation computation.

The active contour may restrict the area in which the image-based search or template matching search will occur and the active contour may provide a seed or initiation for the orientation of a template. Once an active contour is created and the active contour is tracking the elongate instrument in the image, the image-based or template matching search may be performed to track specific features, markers or points of interest on or coupled to the elongate instrument. Features, markers or points of interest may include, e.g., an articulation section, control ring, elongate instrument tip or a sheath. In certain variations, where a template matching search is performed templates may vary based on the type and size of the specific feature, marker or point of interest on the elongate instrument being tracked. The template matching search may be a low computation search that may not take into consideration every single pixel value or all possible locations of the template match.

The active contour tracking and/or the image-based search may facilitate or allow for instinctive driving of the elongate instrument. For example, the active contour tracking and/or the image-based search may allow the user to track or know the heading direction of the elongate instrument or an articulation section of the elongate instrument, or to track or know the direction of articulation of the elongate instrument, which facilitates or allows for instinctive driving of the elongate instrument, e.g., of a robotically controlled elongate instrument or catheter.

Instinctive driving involves the tip of an elongate instrument, e.g., a catheter, moving in the same direction as the command input motion irrespective of the headed direction or orientation of the catheter tip. In order to have instinctive driving for all catheter configurations, the system needs to know the heading direction and rotational orientation of the tip of the instrument at all times or substantially all times, so that it can translate the user input commands accordingly to give the desired output. For example, if a catheter tip is straight inside the body, then a user command to bend left will cause the robotic system to pull the left pull wire or control wire, and the catheter tip will bend left. If the catheter tip has rotated 90° in the clockwise direction inside the body, then when the user commands a left bend, if the robotic system were to pull the left wire, the catheter tip would bend upward. If, however, the robotic system knows the orientation of the tip, then the system will know that it needs to pull on the down wire to get the tip to move left according to the users input.

In certain variations, a low resolution spatial filter or other filter may be used to filter out high frequency texture and/or noise in an image. A particle filter may be used to maintain multiple tracking hypotheses in order to overcome any unnecessary obscuring or blocking of a feature, marker or point of interest of the elongate instrument being tracked in an image. In certain variations, a particle filter may be used to guide template matching. Various images or imaging systems may be utilized to obtain, receive or otherwise display an image. The images may include a fluoroscopy image, 3D image or model or any other image or imaging technology suitable for use in medical procedures.

In certain variations, the active contour may track one or more edges of the elongate instrument in the image. For example, the active contour may specifically track two edges or lines with a darker area between the edges corresponding to the shaft of the elongate instrument. Spacing may be maintained between at least two points in a sequence of points making up the active contour and the spacing may prevent the active contour from mis-tracking, e.g., in areas where the elongate instrument curves rapidly.

In certain variations, the active contour may be updated by using an iterative approach. For example, the active contour may be updated by using one or more iterations or wherein each iteration refines the location of the active contour to the image. Any number of iterations may be used.

The active contour may grow and shrink as a projection of the elongate instrument on the image grows and shrinks, thereby tracking the elongate instrument. Points may be added or removed at a desired distance from an end point of the active contour in the direction that the active contour is traveling to grow or shrink the active contour, in order to track movement of the elongate instrument. Each point along an active contour may produce a fitness value that can guide whether or not that point is on or aligned with the elongate instrument in the image.

In certain variations, an active contour may be initialized by selecting two or more points along a shape or path of the elongate instrument in the image using a pointing device, a touch screen or other selection mechanism. For example, an active contour may be initialized by identifying points on a leader, control ring marker, a sheath marker or other portion of the elongate instrument or sheath. The points may initialize the contour and provide a starting location for tracking a leader, control ring marker, sheath marker or other portion of the elongate instrument or sheath.

In certain variations, a correlation matching search may be performed along the active contour to track features or specific points of the elongate instrument and to enhance or confirm accuracy of the active contour.

In certain variations, one or more secondary active contours for tracking elongate non-instrument objects may be provided. The elongate non-instrument objects may be artificially removed from the image if desired.

In certain variations, a portion of one or more non-elongate non-instrument objects may be tracked within the image using one or more other computer vision technologies such as pattern matching, optical flow, feature matching, or shape matching. The non-elongate non-instrument objects may be artificially removed from the image if desired.

In certain variations, more than one elongate instrument object may be attracted by using more than one active contour. Each active contour may be tracked independently of the other active contours.

In any of the elongate instrument tracking variations described herein, a tracking view may be overlaid on a fluoroscopy image or other image, and a user's view of the image may be augmented or modified to best visualize and track the elongate instrument.

In another variation of a method of tracking a robotically controlled elongate instrument in real time in an image, a first active contour of at least a portion of the elongate instrument or a flexible elongate instrument body may be created, where the active contour tracks the elongate instrument. A template matching search may be performed along the active contour for tracking features of the flexible elongate instrument body. A second active contour for tracking elongate non-instrument objects such as wires, stents, or surgical sutures may also be created. The elongate non-instrument objects may be artificially removed from the image. The image may be a fluoroscopy image or other image as described herein.

In another variation, a method of tracking a robotically controlled elongate instrument in real time in an image may include identifying a sequence of points to initialize an active contour of at least a portion of the elongate instrument. The active contour may be updated as the elongate instrument moves by performing a focused pixel intensity or density search. A template matching search may be performed along the active contour to track features of the elongate instrument and to enhance or confirm accuracy of the active contour. Movement of the elongate instrument may be controlled with one or more robotic commands via a robotic controller and/or robotic instrument driver. Movement of the elongate instrument may be predicted based on previous robotic or system commands, where the robotic or system commands are taken into consideration or are used as factors in predicting the location or movement of the elongate instrument in the image to help with accurately tracking the elongate instrument.

In certain variations, a method of tracking a robotically controlled elongate instrument in real time in an image may include one or more of the following steps: controlling movement of the elongate instrument with a robotic or system command; creating an active contour of the elongate instrument; updating the active contour as the elongate instrument moves; performing a template matching search along the active contour to track features of the elongate instrument; and predicting elongate instrument movement based on the commanded elongate instrument motion to increase tracking accuracy. A command for elongate instrument motion may be utilized to predict where the elongate instrument will be moving in the image. A command for elongate instrument motion may be utilized to predict a location or shape of the active contour in the image. A command for elongate instrument motion may be utilized to focus a pixel density search to update the active contour and/or to focus a template matching search to track features of the elongate instrument in the image. A command for elongate instrument motion may be utilized to eliminate false positives during tracking.

In certain variations, a known distance between a first point and a second point on an elongate instrument may be used to guide or focus a template matching search for the first point based on the position of the second point. A command for elongate instrument motion may be utilized to give guidance on the scale of pixels per millimeter on an image and/or to give guidance on the amount or distance that an elongate instrument is moving out of plane.

Exemplary Systems and Methods for Tracking an Elongate Instrument

Figure 17:
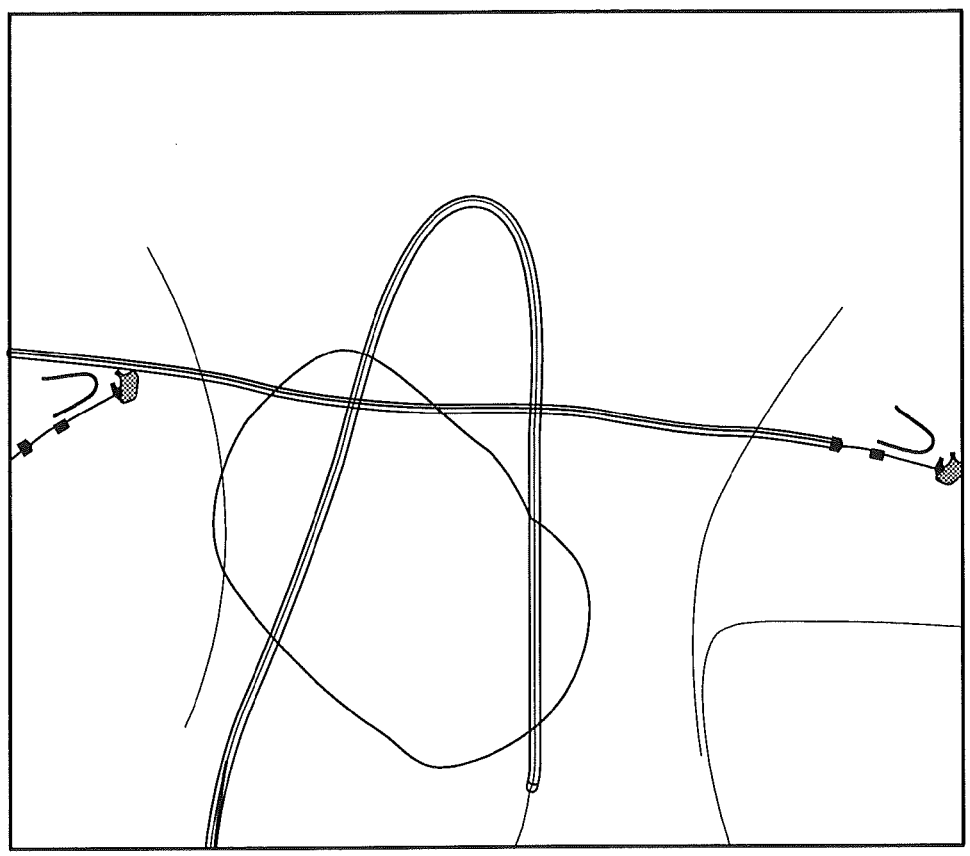
FIG. 17 illustrates a raw fluoroscopic image.

FIG. 17 shows a sample fluoroscopy image that is the source image for other figures described herein. FIGS. 18 through 21 show various components or steps of a variation of a system or method for tracking an elongate instrument.

Figure 18:
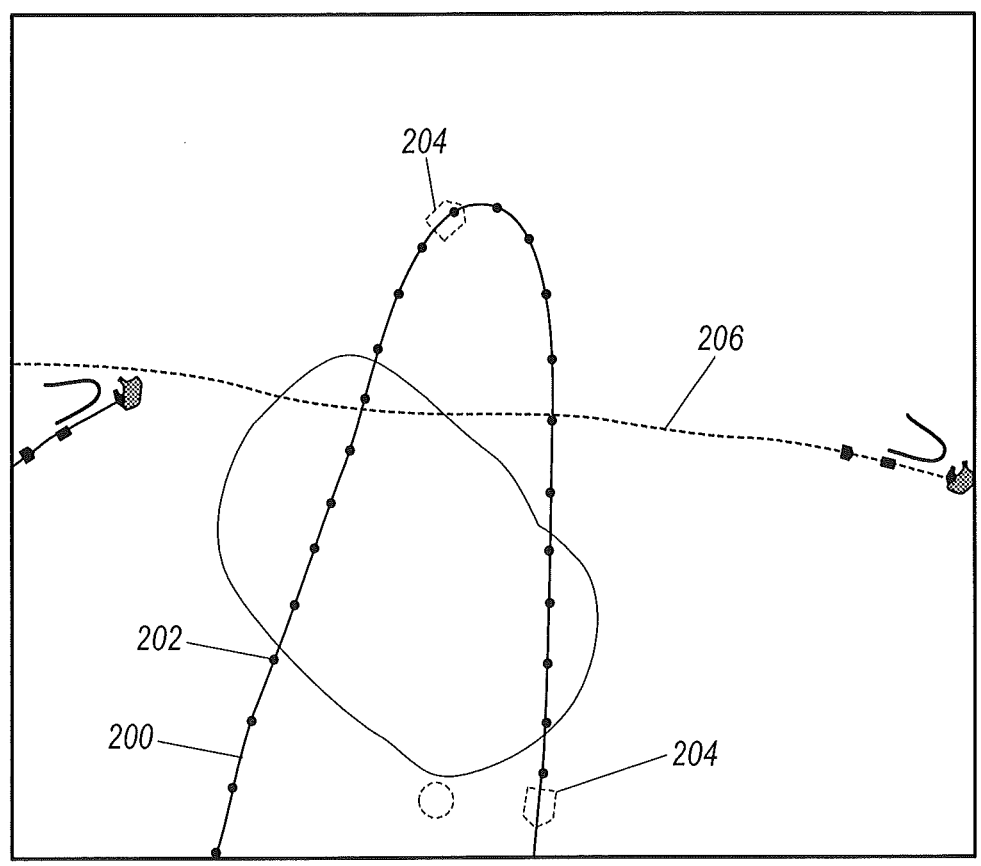
FIG. 18 illustrates an active contour tracking an elongate instrument.

FIG. 18 shows a visual representation of the tracked information overlaid on a representation of the fluoroscopy image (e.g., within the robotic system visual application. The view shows a solid line 200 following the track of the elongate instrument, solid points 202 denoting the nodes of the active contour, and two dashed pentagons 204 showing the location of a sheath and leader control rings along with their orientation direction. There is also a dashed horizontal line 206 showing the tracking of an elongate non-instrument that is rejected when tracking the elongate instrument. Elongate instrument tracking may provide vision tracking of the elongate instrument in a fluoroscopy or other view. It may provide localization in at least two dimensions, including orientation in the plane that can be used to guide instinctiveness and to augment other localization techniques. Throughout this application, an elongate instrument may include a catheter, guidewire, probe or other medical instrument.

In certain variations, elongate instrument tracking may be performed using an active contour ("snake") that tracks at least a portion of the elongate instrument, e.g., the shaft or articulation section, in an image, e.g., a fluoroscopy image. An active contour is a curvilinear model that attempts to minimize an energy function between the shape and the image. The active contour may delineate an outline of the elongate instrument in an image. Identifying, selecting and/or maintaining a set of points (or nodes) on a curve by minimizing an energy function may create an active contour. Terms of the energy function may maintain the spacing between the points of an active contour, minimize curvature (since elongate medical devices may resist sharp bends and may typically remain straight), and/or maintain proximity to the curve or shape of the elongate instrument in the image. In one example, an energy function or algorithm may be used to maintain the spacing between points or nodes. For example, an energy function may be in the form of a cost function or algorithm, such that when two points or nodes move closer together, the cost or risk increases, and the distance between the points is lengthened, increased or maintained by the cost function or algorithm.

In another example, the energy function may be an arbitrary function that provides a penalty if points or nodes move too close together and the function causes a first point or node to be pushed away or forced apart from a second point or node to improve the accuracy of the tracking of an elongate instrument. The spacing between points or nodes of an active contour may also be maintained or controlled to prevent the active contour from mis-tracking in areas where the elongate instrument curves rapidly. The end result is a sequence of points that tracks the elongate instrument or flexible device and grows or shrinks as a projection of the elongate instrument grows and shrinks.

An active contour may be designed to track one or more edges, e.g., edges of an elongate instrument, in an image, using an energy term or function. The energy term or function may be minimized when the active contour is on an edge or when the active contour is on two edges of an elongate instrument. A darker area may be visible on the image, inside or in between the two edges.

In certain variations, an energy function term that maintains spacing between nodes or points of an active contour may automatically space the nodes out in an optimal or desired manner or degree. In other variations, if a node or point of an active contour moves too close to an adjacent node or point, the nodes or points may be combined to maintain good contour coverage. If two nodes or points get sufficiently far from each other, a new node or point may be created or identified between the two nodes or points. These techniques may help maintain the active contour node or point spacing at an adequate, even or desired distance, and may prevent the active contour from malfunctioning or mis-tracking in areas where the elongate instrument curves rapidly or quickly.

In certain variations, elongate instrument tracking may be carried out on an image that has been normalized with a medium-pass filter. Certain dark or light regions that take up a large portion of the image can be filtered out by subtracting the results of a low pass filter from the original image. For example, referring to FIG. 17, the large dark area (the bladder) is filtered out in the processed image in FIG. 20. Likewise, filtering can remove the high frequency noise that manifests itself as speckles and texture due to the imaging device.

In certain variations, various filters, e.g., such as the second derivative of the Gaussian, may be used to detect the shape of an elongate instrument or a catheter in an image, e.g., a fluoroscopy image. The local ridge-like structure of the catheter in an X-ray image is characterized by the direction of flow of the ridge and the thickness of the catheter ridge structure. The second derivative of the Gaussian may be used to analyze such ridge-like structures via the construction of the Hessian matrix and the spectral analysis of this matrix. Using the accurate form of the second derivative of the Gaussian may require computations that are proportional to the size of the catheter in the image. This computational challenge can be overcome using filters that approximate the second derivative of the Gaussian. The computational load is independent of the size of the catheter in the image. The approximate second order Gaussian derivatives can be approximated using piecewise constant filters. See FIG. 23.

Figure 23:
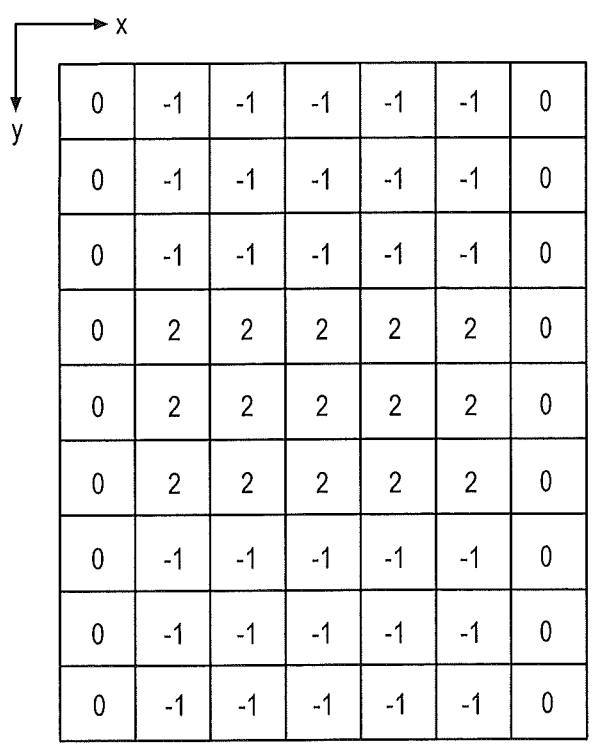
FIG. 23 illustrates use of a filter such as the second derivative of Gaussian.

As shown in FIG. 23, approximate second derivative of Gaussian filter may be in the YY direction. Corresponding filters may be generated for the XX and XY case. Regarding approximate second derivative of Gaussian filter, generally the entries in the kernel are 0, W, and −W/2. Shown in FIG. 23 is the case where W=2. As the smoothing in the underlying Gaussian increases, the filter size increases. The computational efficiency of the filtering can be made independent of the Gaussian smoothing by the use of accumulator images. The smoothing parameter of Gaussian (in pixels) may be equal to the width of the catheter in the image.

Initializing the Active Contour

Tracking a robotically controlled elongate instrument using an active contour may include identifying one or more or a sequence of points to initialize or create an active contour of at least a portion of the elongate instrument. There are various approaches for initializing an active contour, or specifying one or more points or nodes that define where to start searching for the active contour. The selection or identification of one or more points or nodes to initialize an active contour to track at least a portion of an elongate instrument or to track the shape of an elongate instrument may be performed manually or automatically.

In one variation, each node along the active contour may be identified or selected by the user. For example, this may be accomplished by providing a mouse or trackball click or selection using a touch interface, once for each desired node along the active contour. Other identification or selection mechanisms may be utilized as well, e.g. performing gestures using a touch screen or other user interface to trace over a shape of the elongate instrument in an image. This may produce a robust initialization because each selection point may become a node, but this approach requires the necessary user interaction to select or identify each point.

In another variation, a less intensive method to produce a robust initialization of an active contour includes the user making a selection or identification (e.g., clicking) on one or more instrument features or markers (e.g., control ring on a catheter). This may provide two nodes to initialize the active contour and also provides a starting location for tracking those features, i.e., the leader catheter marker and a sheath marker. After these initial selections or clicks, the active contour tracking system may iterate on the same image until the active contour stops lengthening. This automatically locates both extremes of the elongate instrument, e.g., a catheter, at initialization.

It may also be possible to select or click on a single point or node and then search in the area to find the location or orientation of the elongate instrument, e.g., a catheter, by looking at nearby image intensity gradients. This may be less robust than selecting or identifying two points (e.g., by clicking twice), but is often easier to deal with as a user. This may allow for automatic searching methods to be used that find the areas that appear to be catheter markers and then trying to grow the active contour of the catheter from that position, e.g., for a tracking system that does not require user input to initialize. This may also allow automatic recovery if the tracking was interrupted. In this case, finding the markers on the leader and sheath may be carried out with a separate image-based search or template matching search once the catheter path is initialized.

In certain variations, a search algorithm may be used to create an active contour. A user may select a point on an elongate shaft in an image, thereby seeding a search algorithm. The search algorithm may search in the area around the point to update the active contour and the search algorithm may automatically track the elongate instrument once the initial seeding takes place. In certain variations, a Kinematics based state estimation may be utilized. One of the advantages of having a controlled catheter system is that the current state/shape of the catheter may be estimated using kinematic models. The knowledge of the kinematic model and the geometry of the imaging system can be used together to perform a template based matching/verification system. Given that the catheter has been commanded to move to a position in 3D, the registered geometry of the C-Arm may be used to project the 3D shape onto the image. Such a projection can be used to either specify seed points for a segmentation methodology or may be used standalone as a template based matching system. Given some information about the physics of the imaging system, view dependent templates for the catheter can be generated on the fly for use in tracking the catheter. Another use for kinematics assisted segmentation/tracking is to resolve ties when more than one catheter is present in the field of view.

Updating the Active Contour

Figure 21:
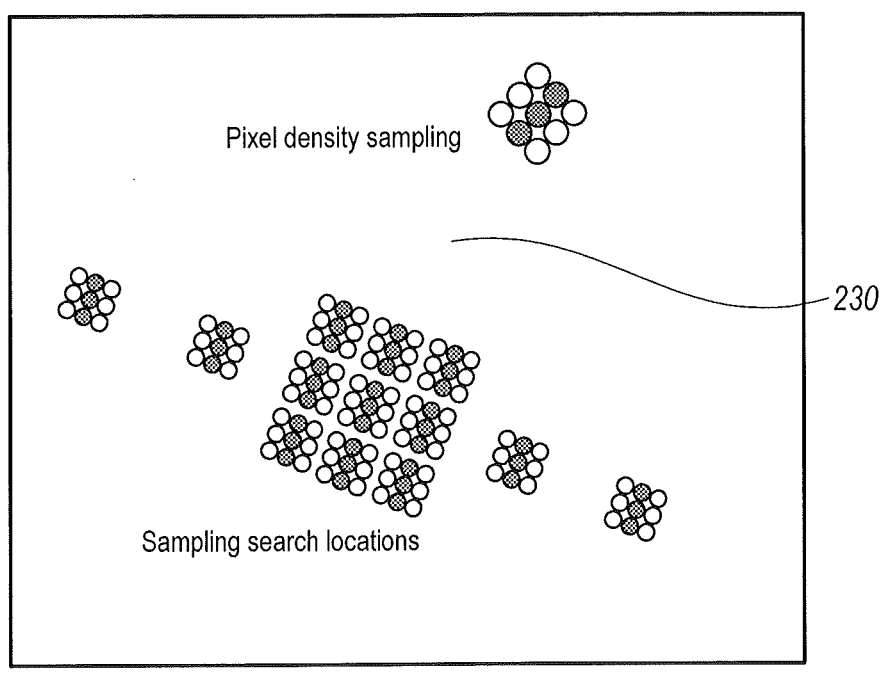
FIG. 21 illustrates a variation of a pixel sampling strategy around each node in an active contour.

Tracking a robotically controlled elongate instrument using an active contour may include updating the active contour as the elongate instrument moves by performing a pixel density or intensity search, focused pixel density or intensity search, color intensity search or other search. This may optimize the shape of the active contour. This sampling search involves sampling a number of points based on the previous position and orientation of the node that is being updated. The lower portion of FIG. 21 depicts some of the positions that may be searched as candidates for each node of the active contour 230. The local area around the previous location of a node may be searched relatively densely and the positions orthogonal to the active contour may be searched on both sides to better detect when the elongate instrument moves side to side in the image. This limited or focused search produces good tracking results while decreasing the amount of computation needed for the search.

For each position in the sampling search, a low-computation method may be used to detect a good fit of the position in the image to the active contour. For example, a set of 9 or more points may be measured (9 points are pictured in the upper portion of FIG. 21), some that are expected to be dark (in the center of a catheter, or in the walls) and some that are expected to be light (on both sides of the catheter). By comparing the expected value to the actual value, a numerical measure is produced (a "fitness" value) that can determine the best position in the sampling search. This is essentially a low-computation template matching (or correlation matching) approach. Also, multiple catheter widths may be searched when performing this optimization to better fit the differing appearances of a catheter. A helpful result of searching multiple widths is that an approximate map of the instrument or catheter widths along its path is created, which may help with localizing features of the instrument or catheter.

In other variations, advanced approaches may be used to match the active contour to the patterns created by the walls of the instrument or catheter.

In certain variations, tracking an elongate instrument (e.g., robotically controlled elongate instrument or catheter) using an active contour may include using an iterative approach to update the active contour, e.g., when presenting a new image frame. In certain variations, a set or maximum number of iterations, e.g., 5 or 10, may be used, but if the contour moves very little between updates, less than the maximum may be needed.

The active contour may grow or shrink as the elongate instrument in the image, on the screen or display, moves, grows, and/or shrinks. Each point or node along the active contour may produce a certain 'fitness value' based on the sampled pixels at that location when doing the low computation image-based search or template matching described above. The population for every node along the elongate instrument produces guidance on the best and worst values that correspond to the active contour tracker node positions. When normalized according to the population of points along the active contour, these fitness values can guide whether a point or node is on the elongate instrument or not on the elongate instrument. At each iteration, extra candidate nodes or points may be created at the desired distance from the end nodes or points of the active contour in the direction that the active contour is traveling in that area. If, after optimization, the fitness value of the end nodes or points are too small, the nodes or points may be removed. If the fitness values are not too small, the nodes or points may remain the active contour and the overall active contour may lengthen.

In certain variations, the nodes on the inside of the active contour (not on the ends) may be in positions that are not along the elongate instrument in the image. When this occurs, if multiple nodes or points within the active contour have a low fitness value, the active contour may be split into two sides and the shorter side of the active contour (or the side of the active contour that does not contain the features of the elongate instrument being tracked) may be deleted from the active contour. This keeps the active contour tracking robustly even when fast motion occurs, such as withdrawing a guide wire. It also helps the active contour to recover from mis-tracking.

Image-Based Search or Template Matching

In certain variations, elongate instrument tracking may also include performing an image-based search, e.g., a template matching search or focused template matching search, along the active contour to track features of the elongate instrument, e.g., to enhance or confirm accuracy of the active contour or to locate a specific feature of the elongate instrument. Various features of or coupled to an elongate instrument, e.g. a catheter, may be tracked. These may include a control ring, articulation section, various catheter markers, a sheath and/or other features.

Figure 19:
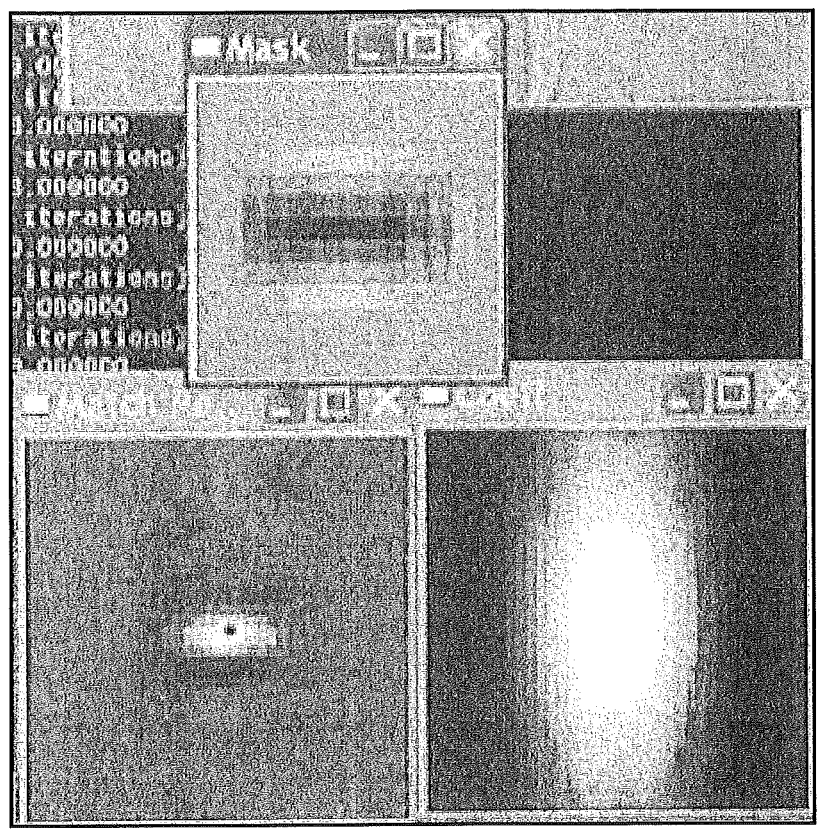
FIG. 19 illustrates various displays showing templates, template matching, and coefficients along an active contour.
Figure 20:
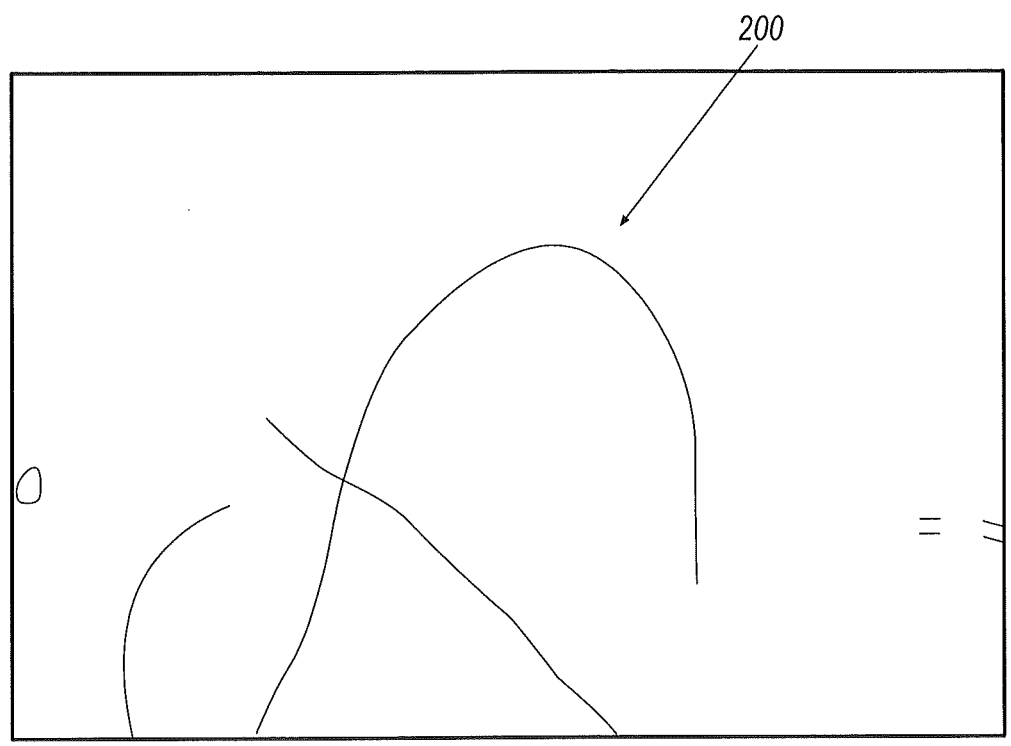
FIG. 20 illustrates a processed image showing filtering and removal of tracked elongate non-instrument members.

Once an active contour is tracking the catheter, templates (or masks) may be used to track features on the catheter, e.g., the control rings on the leader and/or the sheath. Referring to FIG. 18, the pentagons 204 surround the areas in which the template matching occurs. Referring to FIG. 19, the "Mask" window 220 shows the template mask that is suited for the leader catheter. The templates may vary based on the type and/or size of the feature or marker on the elongate instrument. Template matching may be performed along the active contour to find or locate a feature or the orientation of a feature of an elongate instrument. A template matching search may be performed to update the active contour, where the active contour is compared to a known template. Template matching may also be used to identify a specific elongate instrument when other elongate instruments may be visible in the same image.

An advantage of using the combined approach of an active contour and an image-bases search, e.g., a template matching search, is that the active contour restricts the area in which template matching needs to occur and gives a seed or initiation for the orientation of the template. This may significantly speed up the algorithm for real-time tracking and provides additional robustness or accuracy. To combine knowledge of the various tracking techniques, a coefficient mask (see the "Coeff" window of FIG. 19) may be used to weight the template matching results. This mask may be weighted most highly in the center of the active contour and along the path of the active contour. The result of the template matching with these coefficients produces the output in the "Match Re . . . " window in FIG. 19. Finding the most likely candidate in the updated image for the tracked feature may be accomplished by finding the maximum value in this matching image.

Various fluoroscopy machines or systems may have a different pixel to real world distance ratio, and therefore, it may be important to be able to specify the number of pixels in a fluoroscopy image or scene for each millimeter. Furthermore, if a fluoroscopy system is used to zoom in on certain areas of a detector or active contour tracker, it is important to update the pixels/mm ratio for the tracking system. There are various ways to detect these ratios automatically or maintain multiple template matching or pixel density or intensity searches at different resolutions at the same time, when tracking an elongate instrument or catheter.

Predictive Tracking

In certain variations, predictive tracking of the elongate instrument in an image based on known robotic commands or system commands may be performed. An advantage of tracking a robotically controlled system, e.g., the Hansen VCCS system, is that the commands for the elongate instrument motion may be exploited to increase the accuracy of tracking. For example, if the catheter leader or distal articulation section is commanded to move forward two millimeters between frames, the next elongate instrument tracking update may know to base image-based searching or template matching two more millimeters along the elongate instrument. This may save significant computation time because less area needs to be searched and the overall robustness of the tracking may be increased because fast commanded motions may automatically be compensated for by the elongate instrument tracking. Commanded robotic elongate instrument motion may be incorporated into the tracking methods or used by the tracking systems as an indicator of or to predict where the elongate instrument will be moving in an image, where the active contour may be and/or where to focus a pixel density or intensity or template matching search. The known commanded motion may be used to update the active contour more quickly and more accurately. Utilizing the known commanded motion in elongate instrument tracking may help eliminate false positives.

Predictive tracking may use the elongate instrument insertion or retraction information to guide a pixel density or intensity or image-based or template matching search. The use of system or robotic elongate instrument commands in predictive tracking may also allow for more advanced searching techniques that can exploit the relationship between different parts of an elongate instrument. For example, the robotic system may know the distance between the sheath and leader control rings. This distance may be used to guide or focus the search for one of the control rings (markers) based on the position of the other control ring. Also, the distance between the rings or other parts of an elongate instrument, measured in the image space, can give guidance on the scale of pixels per millimeter and/or the amount or distance that the elongate instrument is moving out of plane. For example, the known distance between two points on an elongate instrument may be used to determine whether an active contour is in or out of plane. If the distance along the contour on the image is less than the known commanded distance between the 2 points, then it is known that the image is not showing the true length of the catheter and so this section of the catheter is not lying in the plane that is perpendicular to the image. The known distance may also be used to confirm the scale of the active contour in the image.

In certain variations, a commanded motion of an elongate instrument and the tracked motion of the elongate instrument may be used to localize the elongate instrument roll in the image in order to provide or allow instinctiveness or instinctive driving of the elongate instrument. Other techniques for enhancing or improving elongate instrument tracking may include using a two dimensional or three dimensional roadmap or CT image to help the elongate instrument tracking system to track reliably. In another variation, algorithms may be utilized which allow a tracking system to automatically find elongate instruments in an image without requiring a point on the elongate instrument to be selected or clicked on.

Many predictive tracking techniques such as the heuristics discussed herein may exploit knowledge of robotic or system commands and commanded elongate instrument motion. In certain variations, probabilistic methods such as particle filters may be utilized which allow multiple, multi-modal hypothesis to be maintained in a high-dimensional space. For example, when tracking the location of the leader and sheath markers (control rings) along an active contour, if there is a known distance between the two markers, there is a group of possible positions that may be plausible. If something in the fluoroscopy or image field obscures one of the markers (such as the bladder), there may be a distribution of possible locations for the marker; however, if the other marker is still being tracked, that may restrict the possibilities for locations for the first marker. In cases of mistracking, multiple hypotheses may be tracked simultaneously until more information provides the needed impetus to disqualify one of the hypotheses.

Probabilistic methods such as particle filters may be an effective way to govern the overall elongate instrument or catheter tracking structure. Particle filters could also be used to guide the overall image based search or template matching technique and integrate other, outside information, such as extra markers on a catheter.

In certain variations, methods of tracking and ignoring non-catheter or elongate non-instrument objects that may confuse the system are provided. A method of tracking an elongate instrument, e.g., robotically controlled elongate instrument, in real time in an image may also include creating a second active contour for tracking elongate non-instrument objects. The elongate non-instrument objects may be artificially removed from the image.

Non-catheter objects, e.g., having a linear shape and dark exposure, such as cables or tubes or other monitoring or fluid lines lying on top of the patient may trick the active contour or active contour tracker and/or the template matching into latching onto the wrong object. Therefore, a method for ignoring certain non-catheter objects may be provided. Referring to FIG. 18, the dotted line 206 horizontally across the image is a separate active contour tracker that is tracking a wire in the imaging field. By tracking this object and artificially removing it from the image (see FIG. 20) the tracker may be made robust to non-catheter images.

Not only curvilinear objects, but any object that has features that may be tracked using computer vision methods may be ignored in this manner. This gives the user of the system control over what is tracked and what is not tracked. It can also prevent failure modes of the tracker. In certain variations, the non-catheter objects may be automatically detected and ignored with minimal user input. In other variations, the user may be required to click or select the specific non-catheter object and the system may find the contour related to that object.

Figure 22:
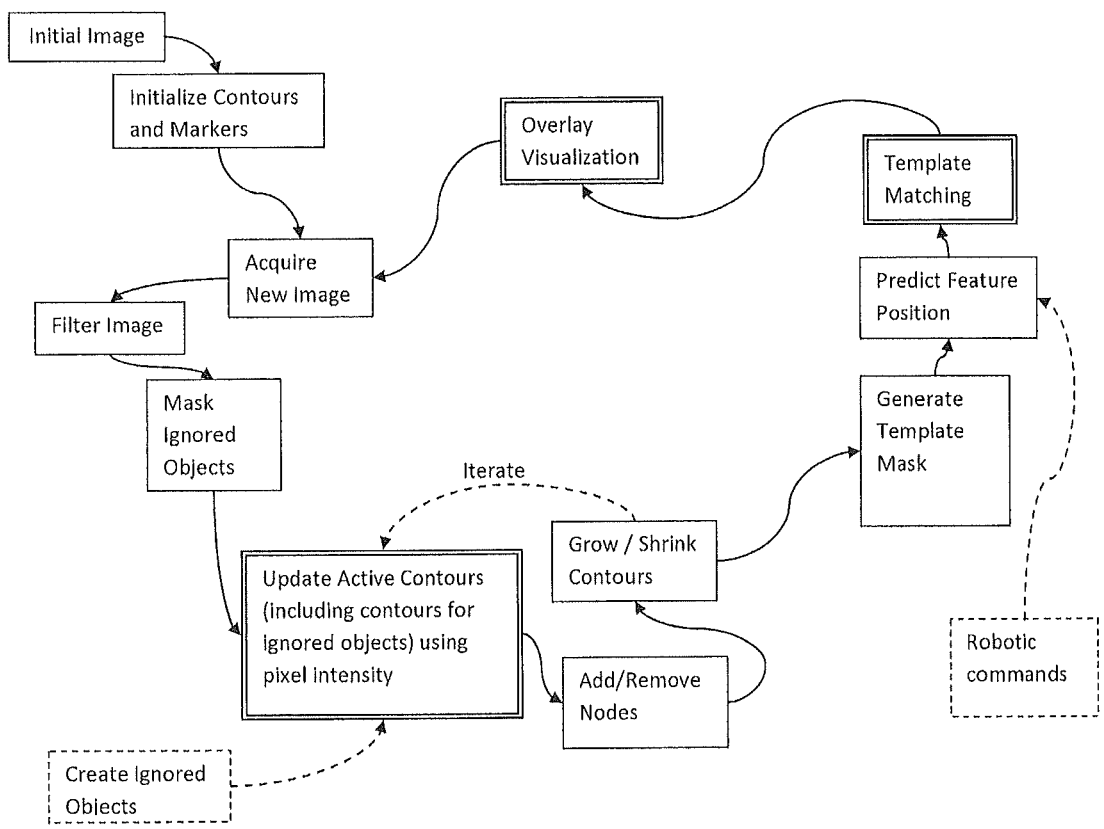
FIG. 22 illustrates a flow chart describing a variation of a process for tracking an elongate instrument.

FIG. 22 illustrates a flow chart describing a variation of a process for tracking an elongate instrument. As shown in FIG. 22, a contour and/or markers may be initialized in an initial image. A new image may then be acquired. The image may be filtered and/or ignored objected may be masked. The active contour may be updated (including contours for ignored objects) using pixel intensity. Ignored objects may be crated. Nodes may be added to the active contour to update the active contour by growing or shrinking. This may be performed in one or more or multiple iterations. A template mask may be generated to predict the position of a feature of an elongate instrument. Robotic commands may be considered in predicting a position of a portion or feature of the elongate instrument or in tracking the elongate instrument. Template matching may be performed along the elongate instrument, e.g., to track one or more features of the elongate instrument and/or to enhance or confirm accuracy of the active contour. Overlay visualization of the contour and/or images may be provided. Methods or systems utilizing one or more of the steps shown in FIG. 22 are contemplated, e.g., any of the various steps may or may not be performed or may be optional.

In certain variations, multiple views may be used either from a biplane fluoroscopy system or from the same fluoroscopy system using different views by rotating the Cann. Multiple fluoroscopy views from different angles acquired using separate fluoroscopy systems or the same system at different times may be used. Multiple views may be used to make it easier to see the different catheters. Multiple fluoroscopy views may be utilized to acquire a third dimension.

In certain variations, multiple view cues may be used to handle the possible distractions to catheter segmentation/tracking algorithms in fluoroscopy images/movies. An example of a distraction is another catheter that crosses the catheter of interest in the image.

Figure 24:
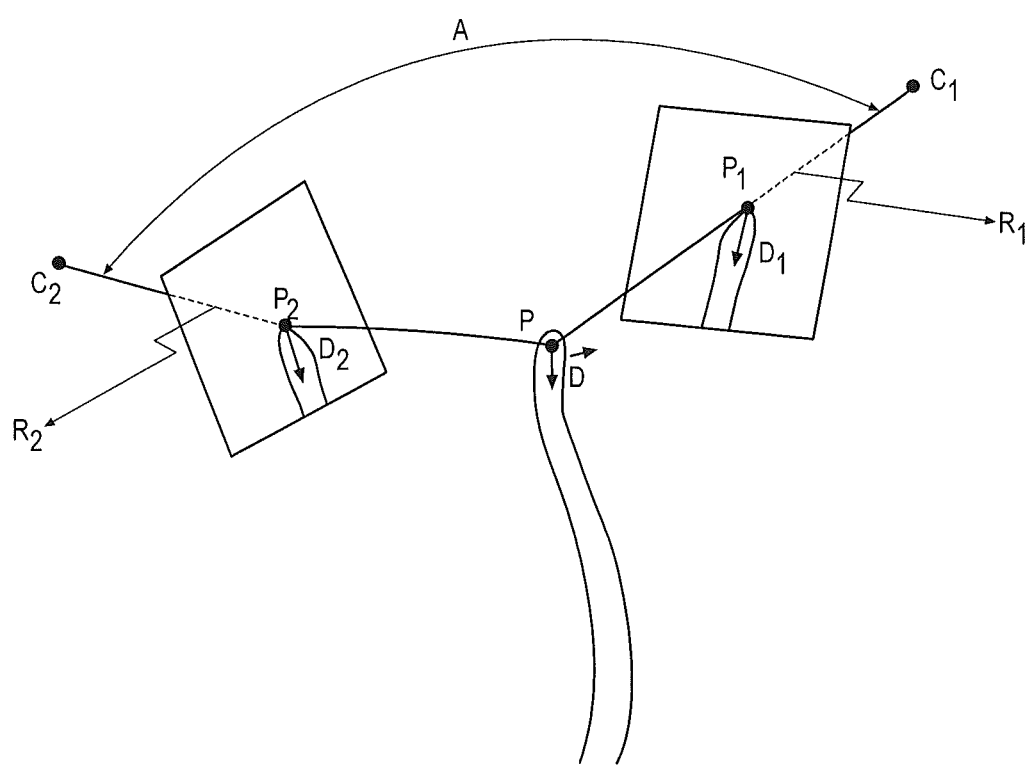
FIGS. 24 and 25 illustrate a system utilizing multiple images.
Figure 25:
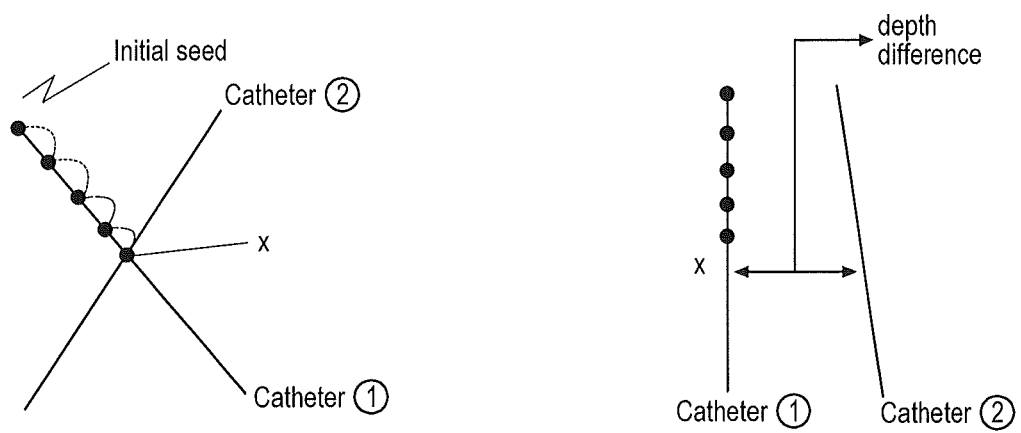

In one example, referring to FIGS. 24 and 25, the provision of a second image may lead to a robust method of segmenting the catheter in the first image. Assuming that the C-Arm geometry is calibrated (G will represent the calibration parameters). P1 and D1 represent a point and direction in image 1. The corresponding representation of these numerical entities in image 2 are represented as P2 and D2. The camera center at position 1 is represented as C1 and in position 2 is represented C2.

The scene with the catheter is imaged from position 1 of the C-Arm to yield image 1. The same scene is imaged from C-Arm position 2 to yield image 2. In the case of a biplane fluoroscopy system images 1 and 2 may be captured simultaneously. When using a single plane fluoroscopy system the second image may be obtained by moving the C-Arm. The angle between the two C-Arm positions, A, is known. Thus given A and G, the image point P1 yields a 3D ray, R1, which passes through C1. This ray can be rotated by an angle A and this would provide the ray, R2, along which P2 must lie. The image point P2 can be estimated by projecting the intersection of R1 and R2. Similarly, given a direction D1 in the image, the corresponding direction D2 in image 2 can be found. In certain variations, it may be assumed that a module is provided, that given a seed point, can provide a quantitative "goodness" measure or reward for moving in a particular direction from the seed point to spatially track the catheter in an image. In certain variations, a multi-view approach may be used for robust initialization of a tracking algorithm and may have applications in the initial alignment of robot and C-arm coordinate frames and in biplane tracking.

FIG. 24 shows a catheter point P being imaged as image points P1 and P2. Given P1, the camera calibration and angle A, the ray R2 can be calculated. Thus, image point P2 can be calculated and image point P1 can be transferred to image point P2. A similar approach may be used to transfer a direction as well.

FIG. 25 illustrates a simple geometric configuration of a crossed catheter and shows how a second image may help handle the case of crossing catheters. When the spatial tracking has reached the crossing point X, there is a potential ambiguity in choosing a direction in image 1 that can be handled by looking at image 2. By choosing path S in image 1 continuity may be maintained in both images, whereas F may lead to a discontinuity in image 2. Thus the second image provides depth cues that can be incorporated to perform the segmentation of the catheter.

For example, a second image of a scene captured from a different viewpoint or C-Arm position may be useful. The second image may help exploit the required depth disparity that may exist between two catheters as two distinct catheters may not pass through the same point in space.

In certain variations, this process may be applied temporally to each image pair from a biplane fluoroscopy system, providing a robust 3D catheter shape tracking system. A variation of this temporal process may include applying the technique only when there is an ambiguity in choosing a direction and not at all times or spatial tracking stages. The same two view concept can be extended to multi-view cases as in rotational/sweep based fluoroscopy-like modalities. Some image processing approaches that detect curvilinear structures in the image can be first applied to the image and an initial set of curvilinear structures can be extracted. Then a catheter segmentation process may be formulated as a strand linking/graph linking problem. The above two view consistency method can be applied during the linking stage as well. The segmentation/shape obtained using the above concept in conjunction with any image processing idea may yields an independent measurement of the catheter shape and can thus be used for closed loop shape control and accurate tip/body positioning.

In certain variations, segmentation for alignment/biplane tracking may be performed by starting out in a first image and obtaining the next step direction and then projecting that direction and the start point to the second view/image. Then, determine if this is a good direction to move in the second image as well. If yes, choose the direction or choose the next best direction to move in the first image, and continue. This may help to overcome crossing catheter problems especially when they are at different depths. The cost that will be maximized/minimized to keep the spatial tracking progressing may depend on agreement from both the images and the individual image-path costs.

Overlaid visualization aides may be provided in any of the systems or methods described herein. One advantage of tracking an elongate instrument overlaid in a fluoroscopy view or other image is the ability to augment the user's view of the fluoroscopy system or image. Instead of requiring the doctor or user to interpret the image, certain things may be automatically interpreted (e.g., such as the location of certain markers on the elongate instrument) and made more visible. This may be accomplished by highlighting the elongate instrument and features as shown in FIG. 18. In other variations, this may be accomplished by: highlighting the active portion of the elongate instrument (e.g., catheter leader or sheath) to augment the user interface and prevent the user from needing to look at the user interface device; detecting when the wire or elongate instrument collides with anatomy or produces too much force; and/or detecting kinks or breakages in the elongate instrument.

Various types of sensors may be utilized for intra-body localization such as electro-magnetic, sonomicrometric, fiber-optic, impedance based, etc. While some of these sensors can obtain measurements with sufficient precision, some may suffer from drift, scaling errors, and other sources of inaccuracy. However, when combined with fluoro, these sensors may become much more useful since fluoro measurements have very high accuracy. Sampling at a low rate in fluoro of e.g., 1 Hz for a 3-hour procedure is approximately equal to 5-minutes of fluoro radiation at a 30-Hz rate, which is a typical clinical frame rate. Therefore, using low-rate fluoro to re-register a catheter equipped with some other localization technology may provide both high accuracy and high precision localization information or tracking information. In addition to fluoro aiding a secondary technology for accuracy, the secondary technology could aid fluoro in tracking by seeding sequential image segmentation procedures.

In certain variations, a method of tracking an elongate instrument in real time in an image may include one or more of the following steps: initializing an active contour in the image where the active contour corresponds to at least a portion of the elongate instrument; and updating the active contour as the elongate instrument moves by performing a search based on pixel intensity to track the elongate instrument.

In certain variations, a method of tracking a robotically controlled elongate instrument in real time in an image includes one or more of the following steps: controlling movement of the elongate instrument with a robotic or system command; creating an active contour which corresponds to at least a portion of the elongate instrument; updating the active contour as the elongate instrument moves; performing an image-based or template matching search along the active contour to track features of the elongate instrument; and/or predicting elongate instrument movement based on the commanded elongate instrument motion to increase tracking accuracy.

In certain variations, a system or robotic system for controlling and/or tracking an elongate instrument with respect to a target space is provided. The system may include a robotic drive system having at least one actuator. The robotic drive system may be configured to interchangeably couple with the elongate instrument to position the instrument with respect to the target space. The system may include a controller configured to initialize an active contour in an image, where the active contour corresponds to at least a portion of the elongate instrument. The controller may be configured to update the active contour as the elongate instrument moves by performing a search based on pixel intensity. The controller can produce a plurality of signals to direct the robotic drive system or elongate instrument in the image frame based on tracking of the elongate instrument with the active contour. The controller may be configured to perform an image-based search along the active contour to track one or more features of the elongate instrument. The image-based search along the active contour may be performed with a template matching search. The controller may be configured to perform an image-based search or template matching search to track a feature, marker or point of interest of the elongate instrument in order to enhance or confirm accuracy of the active contour. The active contour may restrict the area in which an image-based search or template matching search will occur and may provide a seed for the orientation of a template. Once an active contour is tracking the elongate instrument, an image-based search or template matching search may be performed to track a specific feature, marker or point of interest of the elongate instrument to ascertain a location of the specific feature, marker or point of interest on the active contour. A feature or point of interest may include an articulation section, control ring, marker, or a sheath of the elongate instrument.

The controller may be configured to perform tracking and/or an image-based search or template matching search to facilitate instinctive driving of the elongate instrument. The controller may be configured to perform an image-based search or template matching search to track a heading direction of an articulation section of the elongate instrument to facilitate instinctive driving of the elongate instrument. The image may be a fluoroscopy image. The system may also include a low-pass spatial filter for filtering high frequency texture and noise in the image.

The system may include a master input device coupled to the controller, where the master input device uses the active contour or image based search tracking to permit intuitive or instinctive driving of the tool using the robotic drive system. The image may include an image of the target space or patient.

The various systems and methods described herein may, for example, include or utilize any of the systems or methods illustrated in the figures of the present application.

Each of the individual variations described and illustrated herein has discrete components and features which may be readily separated from or combined with the features of any of the other variations. Modifications may be made to adapt a particular situation, material, composition of matter, process, process act(s) or step(s) to the objective(s), spirit or scope of the present invention.

Methods recited herein may be carried out in any order of the recited events which is logically possible, as well as the recited order of events. Furthermore, where a range of values is provided, every intervening value between the upper and lower limit of that range and any other stated or intervening value in that stated range is encompassed within the invention. Also, any optional feature of the inventive variations described may be set forth and claimed independently, or in combination with any one or more of the features described herein.

All existing subject matter mentioned herein (e.g., publications, patents, patent applications and hardware) is incorporated by reference herein its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise, all technical and scientific terms used herein have the same meaning as commonly understood by one of ordinary skill in the art to which this invention belongs.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

While multiple embodiments and variations of the many aspects of the invention have been disclosed and described herein, such disclosure is provided for purposes of illustration only. Many combinations and permutations of the disclosed system are useful in minimally invasive medical intervention and diagnosis, and the system is configured to be flexible. The foregoing illustrated and described embodiments of the invention are susceptible to various modifications and alternative forms, and it should be understood that the invention generally, as well as the specific embodiments described herein, are not limited to the particular forms or methods disclosed, but also cover all modifications, equivalents and alternatives falling within the scope of the appended claims. Further, the various features and aspects of the illustrated embodiments may be incorporated into other embodiments, even if no so described herein, as will be apparent to those skilled in the art.

We claim:

1. A method of tracking a robotically-controlled flexible elongate instrument in real time in an image, the method comprising:
    initializing an active contour in the image, wherein the active contour corresponds to at least a portion of the flexible elongate instrument;
    predicting a next location or shape of the flexible elongate instrument as the flexible elongate instrument is moved, wherein the next location and shape are predicted based on a robotic motion command received at a robotic controller; and
    updating the active contour to track the flexible elongate instrument as the flexible elongate instrument moves, by performing a search based on pixel intensity, wherein a pixel intensity search area is focused based on the predicted next location or shape.

2. The method of claim 1, further comprising performing an image-based search along the active contour to track one or more features of the flexible elongate instrument.

3. The method of claim 2, wherein the image-based search along the active contour is performed with a template matching search.

4. The method of claim 1, wherein an image-based search or a template matching search is performed to track at least one of a feature, a marker or a point of interest of the flexible elongate instrument, in order to enhance or confirm accuracy of the active contour.

5. The method of claim 1, wherein the active contour restricts the area in which an image-based search or a template matching search must occur and provides a seed for the orientation of a template.

6. The method of claim 1, wherein once an active contour is tracking the flexible elongate instrument, an image-based search or a template matching search is performed to track at least one of a feature, a marker or a point of interest of the flexible elongate instrument to ascertain a location of the feature, marker or point of interest on the active contour.

7. The method of claim 6, wherein the feature or the point of interest is selected from the group consisting of an articulation section, a control ring, a marker, or a sheath of the flexible elongate instrument.

8. The method of claim 1, wherein at least one of the tracking, an image-based search or a template matching search facilitates instinctive driving of the flexible elongate instrument.

9. The method of claim 1, further comprising performing an image-based search or a template matching search to track a heading direction of an articulation section of the flexible elongate instrument to facilitate instinctive driving of the flexible elongate instrument.

10. The method of claim 1, wherein the image is a fluoroscopy image.

11. The method of claim 1, further comprising maintaining spacing between at least two points in a sequence of points along the active contour to prevent the active contour from mistracking in areas where the flexible elongate instrument curves rapidly.

12. The method of claim 1, further comprising filtering out high frequency texture and noise in the image with a low-pass spatial filter.

13. The method of claim 1, further comprising filtering out low frequency features comprising at least one of anatomy, imaging artifacts, or elements in the environment with a high-pass spatial filter.

14. The method of claim 1, further comprising performing a correlation matching search along the active contour to track features of the flexible elongate instrument and to enhance or confirm accuracy of the active contour.

15. The method of claim 1, wherein an image-based search or a template matching search is a low computation search using pixel sub-sampling.

16. The method of claim 1, wherein the active contour is updated by using an iterative approach.

17. The method of claim 1, wherein the active contour can grow and shrink as a projection of the flexible elongate instrument on the image grows and shrinks.

18. The method of claim 1, wherein each point along the active contour produces a fitness value that can guide whether or not a point is on the flexible elongate instrument in the image.

19. The method of claim 1, wherein points are added or removed at a desired distance from an end point of the active contour in the direction that the active contour is traveling, to grow or shrink the active contour to track movement of the flexible elongate instrument.

20. The method of claim 1, wherein initializing the active contour comprises selecting two or more points along a shape or a path of the flexible elongate instrument in the image, using a pointing mechanism or a selection mechanism.

21. The method of claim 1, wherein initializing the active contour comprises identifying points on at least one of a leader, a control ring marker or a sheath marker of the flexible elongate instrument, wherein the points initialize the active contour and provide a starting location for tracking the leader, the control ring marker or the sheath marker.

22. The method of claim 1, further comprising performing a template matching search, wherein templates used in the template matching search vary based on a type and a size of a feature on the flexible elongate instrument.

23. The method of claim 22, wherein a particle filter is used to guide the template matching search.

24. The method of claim 1, further comprising maintaining a second contour for tracking other elongate objects and artificially removing the objects from the image.

25. The method of claim 1, wherein one or more computer vision algorithms track elements in the image such as surgical tools, other elongate instruments, or anatomical features, in order to aid the active contour in overcoming the elements overlapping and obscuring the flexible elongate instrument being tracked.

26. The method of claim 1, further comprising:
providing a tracking view overlaid on a fluoroscopy image; and
augmenting a user's view of the fluoroscopy image.

27. The method of claim 1, wherein the image comprises multiple fluoroscopy views from different angles acquired using one or more fluoroscopy systems.

* * * * *